US008486854B2

(12) United States Patent
Berrada et al.

(10) Patent No.: US 8,486,854 B2
(45) Date of Patent: Jul. 16, 2013

(54) POLYSACCHARIDE PHYLLOSILICATE ABSORBENT OR SUPERABSORBENT NANOCOMPOSITE MATERIALS

(75) Inventors: Mohammed Berrada, Montréal (CA); Stéphane Chevigny, Varennes (CA); Claude Thibodeau, Mont St-Hilaire (CA)

(73) Assignee: Archer Daniels Midland Company, Decatur, IL (US)

( * ) Notice: Subject to any disclaimer, the term of this patent is extended or adjusted under 35 U.S.C. 154(b) by 1491 days.

(21) Appl. No.: 10/953,873

(22) Filed: Sep. 29, 2004

(65) Prior Publication Data

US 2005/0214541 A1 Sep. 29, 2005

(30) Foreign Application Priority Data

Sep. 29, 2003 (CA) ..................................... 2443059

(51) Int. Cl.
*B01J 20/00* (2006.01)
(52) U.S. Cl.
USPC ............ 502/404; 502/400; 502/439; 502/402
(58) Field of Classification Search
USPC .................. 424/70.13, 401, 489; 514/54, 60, 514/55, 57; 502/404, 400, 439; 428/311.11, 428/195.1, 311.51, 311.71, 311.91, 317.9, 428/373, 375, 411.1, 500, 522, 913, 402, 428/446, 452; 525/381, 191, 212; 127/11, 127/29, 32, 33; 427/243, 244; 442/104, 127, 442/154, 155, 327, 59; 524/1, 80, 401, 434, 524/501; 526/240; 604/367; 252/1; 71/903; 47/58.1 SC; 119/171, 173; 206/524.6
See application file for complete search history.

(56) References Cited

U.S. PATENT DOCUMENTS

| | | | |
|---|---|---|---|
| 3,706,598 A | 12/1972 | Carrell et al. | |
| 3,935,363 A | 1/1976 | Burkholder et al. | |
| 4,333,461 A | 6/1982 | Muller | |
| 4,454,055 A | 6/1984 | Richman et al. | |
| 4,500,670 A | 2/1985 | McKinley et al. | |
| 4,615,923 A | 10/1986 | Marx | |
| 4,624,868 A | 11/1986 | Muller | |
| 4,629,712 A | 12/1986 | Pinnavaia et al. | |
| 4,914,066 A | 4/1990 | Woodrum | |
| 5,360,903 A | 11/1994 | Lane et al. | |
| 5,419,956 A | 5/1995 | Roe | |
| 5,452,684 A * | 9/1995 | Elazier-Davis et al. | 119/173 |

(Continued)

FOREIGN PATENT DOCUMENTS

| | | |
|---|---|---|
| CA | 2308537 | 11/2000 |
| CA | 2352502 | 1/2002 |

(Continued)

OTHER PUBLICATIONS

Edana, Absorption Under Pressure, 2002, 442.2-02.

(Continued)

*Primary Examiner* — Melvin C Mayes
*Assistant Examiner* — Melissa Stalder

(57) ABSTRACT

The present invention relates to an absorbent or a superabsorbent nanocomposite material comprising a polysaccharide and a phyllosilicate. The polysaccharide component can be a biodegradable polysaccharide that is a self-entangled glass-like polysaccharide or a crosslinked polysaccharide. The phyllosilicate component can be an exfoliation or a semi-exfoliation clay.

36 Claims, 22 Drawing Sheets

U.S. PATENT DOCUMENTS

| | | | |
|---|---|---|---|
| 5,470,964 A | 11/1995 | Qin | |
| 5,489,469 A | 2/1996 | Kobayashi et al. | |
| 5,489,674 A | 2/1996 | Yeh | |
| 5,498,705 A | 3/1996 | Oin | |
| 5,536,825 A | 7/1996 | Yeh et al. | |
| 5,550,189 A | 8/1996 | Qin et al. | |
| 5,583,082 A | 12/1996 | Pinnavaia et al. | |
| 5,718,770 A | 2/1998 | Shah et al. | |
| 5,726,113 A | 3/1998 | Pinnavaia et al. | |
| 5,760,121 A | 6/1998 | Beall et al. | |
| 5,801,116 A | 9/1998 | Cotrell et al. | |
| 5,820,955 A | 10/1998 | Brander | |
| 5,834,391 A | 11/1998 | Pinnavaia et al. | |
| 5,866,645 A | 2/1999 | Pinnavaia et al. | |
| 5,869,033 A | 2/1999 | Schulz | |
| 5,932,017 A | 8/1999 | Chiu et al. | |
| 5,993,769 A | 11/1999 | Pinnavaia et al. | |
| 6,017,632 A | 1/2000 | Pinnavaia et al. | |
| 6,042,839 A | 3/2000 | Lahanas et al. | |
| 6,068,924 A | 5/2000 | Palumbo | |
| 6,096,803 A | 8/2000 | Pinnavaia et al. | |
| 6,124,391 A | 9/2000 | Sun et al. | |
| 6,175,055 B1 | 1/2001 | Schöne | |
| 6,197,849 B1 | 3/2001 | Zilg et al. | |
| 6,228,501 B1 | 5/2001 | Nakazawa et al. | |
| 6,228,903 B1 | 5/2001 | Beall et al. | |
| 6,231,675 B1 | 5/2001 | Chiu et al. | |
| 6,261,640 B1 | 7/2001 | Pinnavaia et al. | |
| 6,271,297 B1 | 8/2001 | Ishida | |
| 6,277,186 B1 | 8/2001 | Shi et al. | |
| 6,294,118 B1 * | 9/2001 | Huber et al. | 264/118 |
| 6,350,711 B1 | 2/2002 | Potts et al. | |
| 6,376,011 B1 | 4/2002 | Reeves et al. | |
| 6,376,034 B1 | 4/2002 | Brander | |
| 6,387,495 B1 | 5/2002 | Reeves et al. | |
| 6,399,690 B2 | 6/2002 | Lan et al. | |
| 6,406,712 B1 * | 6/2002 | Rolf | 424/445 |
| 6,407,155 B1 | 6/2002 | Qian et al. | |
| 6,414,069 B1 | 7/2002 | Pinnavaia et al. | |
| 6,444,653 B1 * | 9/2002 | Huppe et al. | 514/54 |
| 6,451,121 B2 | 9/2002 | Chiu et al. | |
| 6,500,411 B2 * | 12/2002 | SenGupta et al. | 424/59 |
| 6,521,690 B1 | 2/2003 | Ross et al. | |
| 6,579,927 B1 | 6/2003 | Fischer | |
| 6,586,500 B2 | 7/2003 | Bagrodia et al. | |
| 6,716,366 B2 * | 4/2004 | Waldmann | 252/181 |
| 6,730,719 B2 | 5/2004 | Powell | |
| 7,087,669 B2 * | 8/2006 | Ota et al. | 524/493 |
| 2002/0106385 A1 * | 8/2002 | Vatter et al. | 424/401 |
| 2002/0165305 A1 | 11/2002 | Knudson, Jr. et al. | |
| 2002/0169246 A1 | 11/2002 | Barbee et al. | |
| 2003/0022574 A1 | 1/2003 | Pesce et al. | |
| 2003/0060555 A1 | 3/2003 | Lorah et al. | |
| 2003/0095907 A1 | 5/2003 | Pinnavaia et al. | |
| 2003/0095908 A1 | 5/2003 | Pinnavaia et al. | |
| 2003/0134942 A1 | 7/2003 | Lee et al. | |
| 2003/0152531 A1 * | 8/2003 | SenGupta et al. | 424/59 |
| 2003/0225356 A1 | 12/2003 | Kulichikhin et al. | |
| 2003/0228339 A1 * | 12/2003 | El-Nokaly et al. | 424/401 |
| 2004/0035369 A1 | 2/2004 | Marshall | |
| 2004/0106722 A1 | 6/2004 | Haraguchi | |
| 2004/0161435 A1 * | 8/2004 | Gupta | 424/401 |
| 2005/0058672 A1 * | 3/2005 | Gupta | 424/401 |

FOREIGN PATENT DOCUMENTS

| | | |
|---|---|---|
| CA | 2362006 | 5/2002 |
| CA | 2426478 | 10/2003 |
| CA | 2462053 | 9/2004 |
| DE | 196 53 152 | 6/1998 |
| EP | 0 278 601 | 8/1988 |
| EP | 0 087 001 | 1/1995 |
| EP | 1 134 258 | 9/2001 |
| JP | 02-203936 | 8/1990 |
| JP | 04-290547 | 10/1992 |
| JP | 08-092417 | 4/1996 |
| JP | 08-092418 | 4/1996 |
| JP | 09-187493 | 7/1997 |
| JP | 10-244249 | 9/1998 |
| JP | 11-047249 | 2/1999 |
| JP | 2001-120992 | 5/2001 |
| JP | 2001-226525 | 8/2001 |
| JP | 2001-278998 | 10/2001 |
| JP | 2002-035037 | 2/2002 |
| JP | 2002-037924 | 2/2002 |
| JP | 2002-053859 | 2/2002 |
| JP | 2002-253961 | 9/2002 |
| WO | WO 99/29352 A1 | 6/1999 |
| WO | WO 00/21581 A1 | 4/2000 |
| WO | WO 00/35504 A1 | 6/2000 |
| WO | WO 01/32117 A1 | 5/2001 |
| WO | WO 01/34656 A1 | 5/2001 |
| WO | WO 01/91684 A3 | 12/2001 |
| WO | WO 2004/018006 A1 | 3/2003 |
| WO | WO 2004/043663 A2 | 5/2004 |

OTHER PUBLICATIONS

Edana, Centrifuge Retention Capacity, 2002, 441.2-02.

Edana, Free Swell Capacity, 2002, 440.2-02.

Buchholz et al., Modern Superabsorbent Polymer Technology, Wiley-VCH, 1998, ISBN 0-471-19411-5.

Xanthos, Reactive Extrusion Principles and Practice, Hanser, 1992, ISBN 3-446-15677-1.

OECD, ZAHN-Wellens/EMPA Test, OECD Guideline 302B, Adopted Jul. 17, 1992.

Reis et al., Structure Development and Control of Injection Molded Hydroxylapatite-Reinforced Starch-EVOH Composites, Advances in Polymer Technology, V16(4), 1997, p. 263-277.

Tijsen et al., An Experimental Study on the Carboxymethylation of Granular Potato Starch in Non Aqueous Media, Carbohydrate Polymers, 45, 2001, p. 219-226.

Carrado et al., In-Situ Synthesis of Polymer-Clay Nanocomposites From Silicate Gels, Chemistry of Materials, 10(5) 1998, p. 1440-1445.

Carrado et al., Synthetic Polymer-Layer Silicate Clay Composites, Preprints of the 209th ACS Sumposium, 40(2), 1995, p. 310-313.

Pezron et al., Reversible Gel Formation Induced by Ion Complexation, I Borax-Galactomannan Interactions, Macromolecules, V 21(4), 1988, p. 1121-1125.

Dufresne et al., Nanocomposite Materials of Thermoplastic Polymers Reinforced by Polysaccharide, ACS Symposium 723, 1999, p. 39-55.

Darder et al., Biopolymer-Clay Nanocomposites Based on Chitosan Intercalated in Montmorillonite, Chemistry of Materials, V 15(20), 2003, p. 3774-3780.

M'Bodj et al., Plastic and Elastic Properties of the Systems Inserstratified Clay-Water-Electrolyte-Xanthan, J. Colloid and Interface Sco., V273(2), 2004, p. 675-684.

Riccardo, Water-Absorbent Polymers: A Patent Survey, J. Macromol Sci., C34, N°4, 1994, p. 607-662.

Jasinski et al., Boron Equilibra With High Molecular Weight Guar: A NMR Study, J. Polymer Science, Part B, V43(8), Jun. 1996, p. 1477-1488.

Okada et al., Nylon 6-Clay Hybrid, Mater. Res. Soc. Symp. Proc., V 171, 1990, p. 45-50.

Besun et al., Shear Dependent Rheological Properties of Starch-Bentonite Composite Gels, Colloid & Polymer Science, V 275(6), 1997, p. 567-579.

Wilhelm et al., Starch Films Reinforced With Mineral Clay, Carbohydrate Polymers, V 52(2), 2003, p. 101-110.

Wilhelm et al., The Influence of Layered Compounds on the Properties of Starch/Layered Compound Composites, Polymer International, V52(6), 2003, p. 1035-1044.

Wu et al., Study of Starch-Graft-Acrylamide/Mineral Powder Superabsorbent Composite, Polymer, V 44 (21), 2003, p. 6513-6520.

Yu et al., A New Hybrid Nanocomposite Prepared by Graft Copolymerization of Butyl Acrylate Onto Chitosan in . . . , Radiation Physics & Chemistry, V69(6), 2002, p. 467-471.

Fuller et al., Flocculation Coagulation of CA and MG Saturated Montmorillonite in the Presence of a Neutral Polysaccharide, Clays and Clay Mineral, V43(5), 1995, p. 533-539.

(Abstract Only) Chenu et al., Modification in the Textural Organisation of a Calcium . . . , Compte Rendus De L'Académie Des Sciences, V 310(7), 1990, p. 975-980.

McGlashan et al., Preparation and Characterisation of Biodegradable Starch-Based Nanocomposite Materials, Polymer International, V 52(11), 2003, p. 1767-1773.

Ohmura, The Superabsorbent Market, Nonwovens Industry, May 2003, p. 24.

Björnberg, Natural Versus Synthetic Blood in Testing, Nonwovens World, Apr.-May 2000, p. 54-62.

Park et al., Environmentally Friendly Polymer Hybrids, Part 1, Mechanical Thermal and Barrier Properties of Thermoplastic . . . , J. Materials Science, 38, 2003, p. 905-915.

De Carvalho et al., A First Insight of Thermoplastic Starch and Kaolin, Carbohydrate Polymers, V45(2), 2001, p. 189-194.

Wu et al., Synthesis and Properties of Starch-Graft Polyacrylamide/Clay Superabsorbent Composite, Macromol, Rapid Com., V21(15), 2000, p. 1032-1034.

Uyama et al., Green Nanocomposites From Renewable Resources, Poly. Prep. V 44(1), 2003, p. 107-108.

Schott, Bentonite-Cellulose Systems: Flow Behavior of Mixed Dispersions and Mechanical Properties of Composite Films, V 58(10), 1970, 1492-1496.

Park et al., Preparation and Properties of Biodegradable Thermoplastic Starch/Clay, Macromolecular Materials and Engineering, 287(7), 2002, p. 553-558.

Supplemental European Search Report, issued in European Patent Application No. EP 04 786 678.5, dated Jun. 3, 2009.

http://www.intota.com/experts.asp?strSearchType=all&strQuery=superabsorbent+material; visited on Mar. 18, 2011; Copy Right Date 2011.

P.M.Ajayan, L.S.Schadler, P.V.Braun, Bulk Metal and Ceramic Nanocomposites, Nanocomposite Science and Technlology, pp. 1-236, 2003 Wiley-Vch Verlag GmbH & Co. KGaA, Weinheim.

* cited by examiner

POLYSACCHARIDE PHYLLOSILICATE ABSORBENT OR SUPERABSORBENT NANOCOMPOSITE MATERIALS

This application claims priority to co-pending Canadian Application No. 2,443,059 filed Sep. 29, 2003. The entire text of the above application is incorporated by reference.

FIELD OF THE INVENTION

The present invention relates to novel polysaccharide phyllosilicate absorbent or superabsorbent materials, as well as to methods for producing same.

BACKGROUND OF THE INVENTION

Water absorbent materials such as superabsorbent polymers can be employed in various applications, such as in disposable sanitary products (for example, diapers, incontinence articles, feminine hygiene products, airlaids and absorbent dressings), household articles, sealing materials, humectants for agricultural products for soil conditioning, oil-drilling, anti-condensation coatings, water-storing materials in agriculture/horticulture, absorbent paper products, bandages and surgical pads, pet litter, wound dressings, and as chemical absorbents. Furthermore, they can be employed in applications related to the transportation of fresh food or seafood, and in food packaging applications.

The largest use of superabsorbent materials, however, is in disposable personal hygiene products. These products include, in order of volume of superabsorbent material used, diapers, training pants, adult incontinence products and feminine hygiene products. Of these, diapers account for over 85% of the total amount of superabsorbent material sold in 2002 (Ohmura K., *Nonwovens Industry*, 2003, 34(5), p. 24). As a result, the development of superabsorbent materials has been largely focused on the creation of materials having optimal properties for absorbing urine.

The significant differences between the numerous fluids to be absorbed by the various disposable absorbent products, poses a substantial challenge to any manufacturer of hygiene products.

In the case of diapers, the fluid to be absorbed is typically urine, a fluid largely composed of water, salts and nitrogenous materials such as urea. In the case of feminine hygiene products, the fluid to be absorbed is typically menses, a complex fluid comprising water, mucous fluids, salts, proteins, fibrinogens, blood and cell debris (Björnberg, *Nonwovens World*, 2000, 9(2), pp 54-62). In such complex fluids, cells and clotted materials are too large to diffuse into the structural network of the superabsorbent material. Instead, they will adsorb onto the surface of the particles composing the superabsorbent material. Due to the high osmotic pressure of the partially swollen superabsorbent material, the cells and clotted materials will become dehydrated, leading to formation of a nearly impermeable layer surrounding the superabsorbent material. This essentially impermeable layer will seriously impede the efficacy of the superabsorbent material. The nature of the superabsorbent material used for absorbing complex fluids such as menses, should therefore be different from that used for absorbing simple fluids such as urine.

Various approaches have been disclosed regarding the development of superabsorbent materials capable of absorbing complex fluids such as menses. However, any improvement in the ability of these specifically designed superabsorbent materials to absorb complex fluids, was oftentimes offset by a diminishment in their ability to absorb simple fluids. Moreover, these specifically designed superabsorbent materials are often times more expensive in comparison to the mass-produced superabsorbent materials developed primarily for absorbing simple fluids such as urine.

The use of chemically treated superabsorbent materials having an enhanced ability to absorb complex fluids, has been previously described in a number of documents (Potts et al. U.S. Pat. No. 6,350,711; Di Luccion et al. WO 01/91684). While considered to be somewhat effective, these materials often involve complicated manufacturing processes, which invariably increase the cost of the resulting superabsorbent materials.

From the many approaches used to design superabsorbent materials capable of absorbing complex fluids, plant-based polymers, and clays or mineral compounds, have been found to be particularly useful.

There is a global demand for replacing petroleum-derived raw materials with renewable plant-based materials. The use of natural, biodegradable glass-like pregelatinized starches as absorbents for liquids has been disclosed by Le Groupe Lysac (Huppé et al. CA 2,308,537).

It was observed that modified starches could interact synergistically with mannose containing polysaccharides, ionic polysaccharides, gelling proteins or mixtures thereof (Bergeron, Calif. 2,426,478). These synergistic interactions have been found to be especially useful in formulating absorbent materials. The absorption characteristics of these modified starches could be attributed to amylopectin, a high molecular weight branched polymer of glucose. It was found that amylopectin, when crosslinked or networked, provides materials having improved absorbent properties (Le Groupe Lysac; Thibodeau et al. (CA 2,462,053)).

Le Groupe Lysac (Couture et al., CA 2,362,006) has previously disclosed polyethylene glycol crosslinked polysaccharides as being particularly useful absorbents. Other modified polysaccharides having improved absorbent properties have been previously reported by Qin et al. (U.S. Pat. No. 5,550,189; U.S. Pat. No. 5,498,705; and U.S. Pat. No. 5,470,964); Besemer et al. (WO 0035504A1; WO 0134656A1; and WO 9929352A1); Chung-Wai et al. (U.S. Pat. No. 5,932,017; U.S. Pat. No. 6,231,675; and U.S. Pat. No. 6,451,121); Shah et al. (U.S. Pat. No. 5,718,770); Shi et al. (U.S. Pat. No. 6,277,186); as well as by Beenackers A. A. C. M. et al. (*Carbohydr. Polym.*, 2001, 45, 219-226).

The use of galactomanans, crosslinked with borate or zirconium ions, as absorbent polysaccharides, has been disclosed in a number of patents: U.S. Pat. No. 4,624,868; U.S. Pat. No. 4,333,461; JP 2002-253961; JP 2002-035037; JP 2001-278998; JP 2002-037924; JP 2002-053859; JP 2001-120992; JP 2002-053859; and JP 2001-226525. However, these polysaccharides suffer from syneresis and gel flowing problems.

Cottrell et al. (U.S. Pat. No. 5,536,825 and U.S. Pat. No. 5,489,674) disclosed the use of solvent (methanol or isopropanol) purified galactomanans as absorbent polysaccharides. Furthermore, Annergren et al. (WO 0021581A1) disclosed that soaking cross-linkable polysaccharides in methanol provides a material exhibiting superior absorbency. However, the use of alcohols imparts increased process costs in addition to requiring additional environmental precautions.

Even though the use of polysaccharide-based absorbent materials in personal care products is known, they have not gained wide acceptance in such applications. This is due, at least in part, to their absorbent properties being generally inferior to synthetic absorbent materials such as polyacrylates. Furthermore, many of the natural-based materials exhibit poor absorption properties, particularly when subjected to external pressures. Many of the natural-based materials tend to form soft, gelatinous masses, when swollen with a liquid. When employed in absorbent products, the presence of such soft gelatinous masses tends to prevent the passage of liquids (such as physiological solutions or aqueous solutions) through the fibrous matrix in which the absorbent material is incorporated. This phenomenon is known as gel blocking. Once gel blocking occurs, subsequent insults of liquid cannot be efficiently absorbed by the product, and the product tends to leak.

Clays, and other mineral compositions such as diatomaceous earth are environmentally friendly, naturally abundant and economic. Even though many types of clay are known for their liquid absorbing properties, their use is often restricted due to their colloidal, dispersive properties in water. The use of clays in combination with other ingredients such as polymers, has been previously disclosed.

Burkholder et al. (U.S. Pat. No. 3,935,363) disclosed that clay minerals having enhanced water-absorbing properties can be obtained when flocculated into granular aggregates using small amounts of an inorganic salt solution and/or a water-soluble polymeric flocculating agent such as polyacrylic acid, followed by drying.

Physical blends of clays and polyacrylates have also been reported by Shinji et al. (JP 10-244249), Kobayashi et al. (U.S. Pat. No. 5,489,469), McKinley et al. (U.S. Pat. No. 4,500,670), Richman et al. (U.S. Pat. No. 4,454,055), Sun et al. (U.S. Pat. No. 6,124,391), Roe et al. (U.S. Pat. No. 5,419,956), and Schöne (U.S. Pat. No. 6,175,055).

Physical blends of superabsorbents having clay aggregates on their surface to help them absorb physiological fluids have been disclosed by Herfert et al. (US2004018006 A1) and Reeves et al. (U.S. Pat. No. 6,387,495 and U.S. Pat. No. 6,376,011).

A blend of a bentonite clay (>85%) and a water swellable-water insoluble organic polymeric hydrocolloid, having improved absorbency for use in cat litter applications has been disclosed by Woodrum (U.S. Pat. No. 4,914,066). Cat litters comprising borax crosslinked galactomanans and bentonite have been disclosed by Marshall (US20040035369).

A dry blend of kieselguhr (diatomaceous earth) and organic gel formers (CMC, starch, dextrose, gelatin, etc.) for use in absorbent pads for food packaging has been disclosed by Marx (U.S. Pat. No. 4,615,923).

A dry blend including ionic polymers such as sodium carboxymethyl cellulose, ionic crosslinkers and clays has been disclosed by Brander (U.S. Pat. No. 6,376,034 and U.S. Pat. No. 5,820,955). These blends were disclosed as being particularly useful in food packaging applications as absorbent pads.

Polysaccharide-clay physical blends, even though offering synergistic performances with regards their absorption properties, do not possess the absorption capacities of modified polysaccharides or synthetic polymers.

Nanocomposites constitute a relatively new class of materials. As implied by the term "nanocomposites", the constituents making-up the nanocomposite material are of nanometer size; one nanometer being one-millionth of a millimeter. Nanocomposite materials often exhibit properties, reflective of the materials making-up the composite. Nanocomposite materials can be synthesized using surprisingly simple and inexpensive techniques.

Clays are composed of phyllosilicates, also referred to as sheet-like silicates. These silicates have a thickness of about 1 nanometer (nm), while having a length and a width ranging from 300 to 500 nm. The size, composition and shape of phyllosilicates will vary depending on the clay source. Cations such as calcium, magnesium, sodium or potassium ions are located between phyllosilicates, in a "sandwich-type" arrangement. Upon exposure to an aqueous environment, these cations become hydrated, increasing the space between the distinct phyllosilicates, resulting in a swelling of the clay.

Phyllosilicate nanocomposites are materials comprising a nanoscale dispersion of phyllosilicates in a polymer network. Typical phyllosilicate nanocomposites are exfoliated nanocomposites, intercalated nanocomposites and semi-exfoliated nanocomposites.

Exfoliated nanocomposites are also referred to as "phyllosilicate dispersions". Within these exfoliated nanocomposites, the phyllosilicates are delaminated and uniformly dispersed through the polymer network.

Intercalated nanocomposites are also referred to as "sandwich nanocomposites". Intercalated nanocomposites are composed of repeating and alternating phyllosilicate-polymer layers.

Semi-exfoliated nanocomposites are composed of partially exfoliated clays. Within these semi-exfoliated nanocomposites, clays are delaminated into smaller units comprising from about 45 to 70 phyllosilicate blocks. Clays usually comprise units having from about 85 to 140 phyllosilicate blocks as defined by Chenu et al. (*Comptes Rendus de l'Académie des Sciences*, 1990, Série 2, 310 (7 série 2), PP. 975-980). These smaller phyllosilicate units are dispersed uniformly throughout the polymer network.

Nanocomposites can be prepared by numerous techniques. The most common technique involves ion exchange of the cations located in the interlayer spacing of the clays using cationic surfactants (cationic molecules bearing $C_8$-$C_{30}$ aliphatic chains). This technique was first reported by Okada et al. (*Mat. Res. Soc. Proc.*, 1990, 171, 45-50) and subsequently by Pinnavaia et al. (U.S. Pat. No. 6,261,640; U.S. Pat. No. 6,414,069, and U.S. Pat. No. 6,261,640).

Techniques for increasing the interlayer spacing between the phyllosilicates making-up the clays have been disclosed by Beall et al. (U.S. Pat. No. 6,228,903 and U.S. Pat. No. 5,760,121); Lan et al. (U.S. Pat. No. 6,399,690); Qian et al. (U.S. Pat. No. 6,407,155); Zilg et al. (U.S. Pat. No. 6,197,849), Ross et al. (U.S. Pat. No. 6,521,690); Barbee et al. (US20020169246 A1); Ishida (U.S. Pat. No. 6,271,297); Powell et al. (U.S. Pat. No. 6,730,719); Knudson et al. (US20020165305 A1); Lorah et al. (US20030060555 A1); Fischer et al. (U.S. Pat. No. 6,579,927) and Bagrodia et al. (U.S. Pat. No. 6,586,500).

Nanocomposites have also been prepared using physicochemical techniques such as extrusion, lyophilization, and ultrasonic wave treatments, as disclosed by Torkelson et al. (WO 2004043663); Lee et al. (US20030134942 A1); Nobuyoshi (JP 02-203936), and McClelland et al. (CA 2,352,502).

The use of organophilic clays such as activated quarternium-18 bentonite for the absorption and deactivation of fecal proteolytic enzymes, has been disclosed by Schulz (U.S. Pat. No. 5,869,033). These organophilic clays were used to prevent diaper rash.

Hybrid organic-inorganic gels for use in cosmetic or pharmaceutical compositions have been disclosed by Lahanas et al. (U.S. Pat. No. 6,042,839); Udagawa (JP 09-187493); Collin et al. (EP 1327435 A1); and Chevalier et al. (EP 1203789 A1). However, theses gels have not been reported as absorbent materials for use in hygiene related applications.

Starches have also been reported as being used as components in nanocomposite materials. Hydroxyapatite reinforced starch/ethylene-vinyl alcohol copolymer composites have been reported by Reis et al. (*J. Adv. Polym. Technol.* 1997, 16, 263). Calcined kaolin/thermoplastic starch composites have been disclosed by DeCarvalho et al. (*Carbohydr. Polym.* 2001, 45 (2), 189-194). Montmorillonite/thermoplastic starch hybrids have been described by Park et al. (*Macromolecular Materials and Engineering*, 2002, 287(8), pp. 553-558, *J. of Mat. Sci*, 2003, 38 (5), pp. 909-915) and McGlashan et al. (*Polymer International*, 2003, 52(11), PP 1767-1773). However, these starch containing nanocomposite materials were not reported as exhibiting absorbent properties.

The use of chitosan in nanocomposite materials has also been reported. Cationic chitosan, intercalated in montmorillonite, has been disclosed by Darder et al. (*Chemistry of materials*, 2003, 15 (20), PP 3774-3780). A butyl-acrylate-graft chitosan montmorillonite nanocomposite, has been reported by Li et al. (*Radiation physics and chemistry*, 2004, 69(6) APR, PP 467-471). The use of xanthan and scleroglucan in nanocomposite materials has also been reported.

Superabsorbent nanocomposites produced from ethylenically unsaturated monomers have been reported by Eiji et al. (JP 04-290547). Even though having a high absorption and retention capacity, they are made from non-renewable sources and are generally not biodegradable nor hypoallergenic. Polacrylamide nanocomposites have been reported by M'Bodj, O. et al. (*Journal of Colloid and interface science*, 2004, 273(2) (May 15), PP 675-684).

Starch-graft-polyacrylamide constitutes one of the superabsorbents with the highest water absorbency (Riccardo P. O., *Water-Absorbent Polymers: A Patent Survey. J. Macromol. Sci., Rev. Macromol. Chem. Phys.*, 1994, 607-662 (p. 634) and references cited therein). However, due to high production costs and lower gel strength, starch-graft-polyacrylamide applications are limited.

The synthesis and properties of starch-graft-polyacrylamide/clay superabsorbent composites having enhanced absorbent properties, have been reported by Jihuai Wu et al. (*Macromol. Rapid Commun.* 2000, 21, (15), pp 1032-1034, *Polymer*, 2003, 44 (21), PP 6513-6520). However, these composite materials are neither biodegradable nor hypoallergenic.

Unfortunately, most modified polysaccharide-based materials do not possess absorptive properties comparable to many of the synthetic, highly absorptive materials, severely limiting their use as absorbent materials in personal hygiene products.

There thus remains a need for polysaccharide-clay highly absorbent nanocomposite materials suitable for use in personal hygiene products as well as methods for producing these highly absorbent nanocomposite materials.

SUMMARY OF THE INVENTION

The present invention refers to a number of documents, the contents of which are herein incorporated by reference in their entirety.

The present invention relates to novel absorbent or superabsorbent materials. More specifically, the present invention relates to superabsorbent nanocomposite materials comprising polysaccharides and phyllosilicates. Yet more specifically, the present invention relates to superabsorbent nanocomposite materials comprising biodegradable absorbent or superabsorbent polysaccharides and phyllosilicates. The biodegradable absorbent or superabsorbent polysaccharides may be self-entangled in a glass-like pattern and/or may be cross-linked. Moreover, the superabsorbent nanocomposite materials of the present invention are preferably dry, solid materials having good fluid-swelling properties.

In a preferred embodiment, the present invention relates to novel absorbent or superabsorbent polysaccharide-phyllosilicate nanocomposite materials comprising modified galactomanans or starches.

The present invention also relates to the use of the superabsorbent nanocomposite materials comprising polysaccharides and phyllosilicates in disposable sanitary products such as for example, diapers, incontinence articles, feminine hygiene products, airlaids and absorbent dressings. Moreover, the present invention relates to the use of the superabsorbent nanocomposite materials comprising polysaccharides and phyllosilicates in household articles, sealing materials, humectants for agricultural products for soil conditioning, mining and oil drilling, anti-condensation coatings, water-storing materials in agriculture/horticulture/forestry, absorbent paper products, bandages and surgical pads, absorbents for chemical spills, polymeric gels for cosmetics and pharmaceuticals, artificial snow and in fire-fighting techniques. Furthermore, the present invention relates to the use of the superabsorbent nanocomposite materials comprising polysaccharides and phyllosilicates in applications related to the transportation of fresh food or seafood as well as in food packaging applications.

In a further preferred embodiment, the present invention also relates to the use of the superabsorbent nanocomposite materials comprising polysaccharides and phyllosilicates for absorbing liquids, non-limiting examples of which include water, aqueous solutions, physiological fluids and saline solutions.

The present invention also relates to compositions including a superabsorbent nanocomposite material comprising polysaccharides and phyllosilicates, and a co-absorbent material.

Finally, the present invention relates to methods for preparing superabsorbent nanocomposite materials comprising polysaccharides and phyllosilicates.

In yet a further preferred embodiment, the present invention relates to methods for preparing superabsorbent nanocomposite materials comprising biodegradable absorbent or superabsorbent polysaccharides and phyllosilicates.

The use of the word "a" or "an" when used in conjunction with the term "comprising" in the claims and/or the specification may mean "one," but it is also consistent with the meaning of "one or more," "at least one," and "one or more than one." Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that any embodiment discussed in this specification can be implemented with respect to any method or composition of the invention, and vice versa. Furthermore, compositions of the invention can be used to achieve methods of the invention.

The term "about" is used to indicate that a value includes an inherent variation of error for the device or the method being employed to determine the value.

Other objects, features and advantages of the present invention will become more apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

Having thus generally described the invention, reference will now be made to the accompanying drawings, showing by way of illustration a preferred embodiment thereof, and wherein.

DETAILED DESCRIPTION OF THE INVENTION

Figure 1:
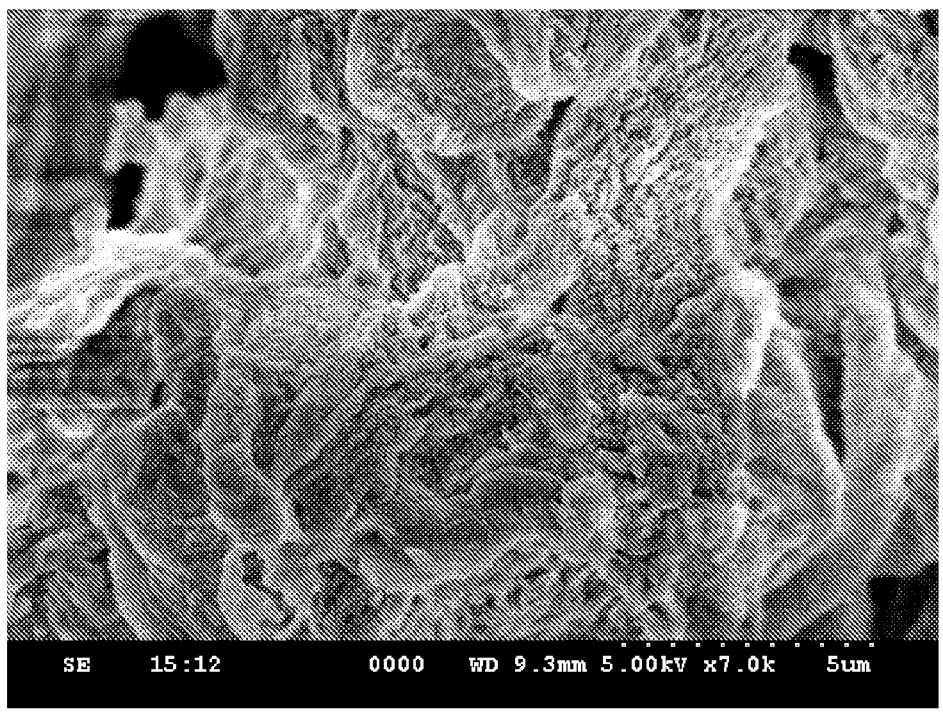
FIG. 1 illustrates a scanning electron micrograph (Magnification 7,000 times) of a 20% (w/w) calcium bentonite (Minelco MB 300)—guar borax nanocomposite (example 7).
Figure 2:
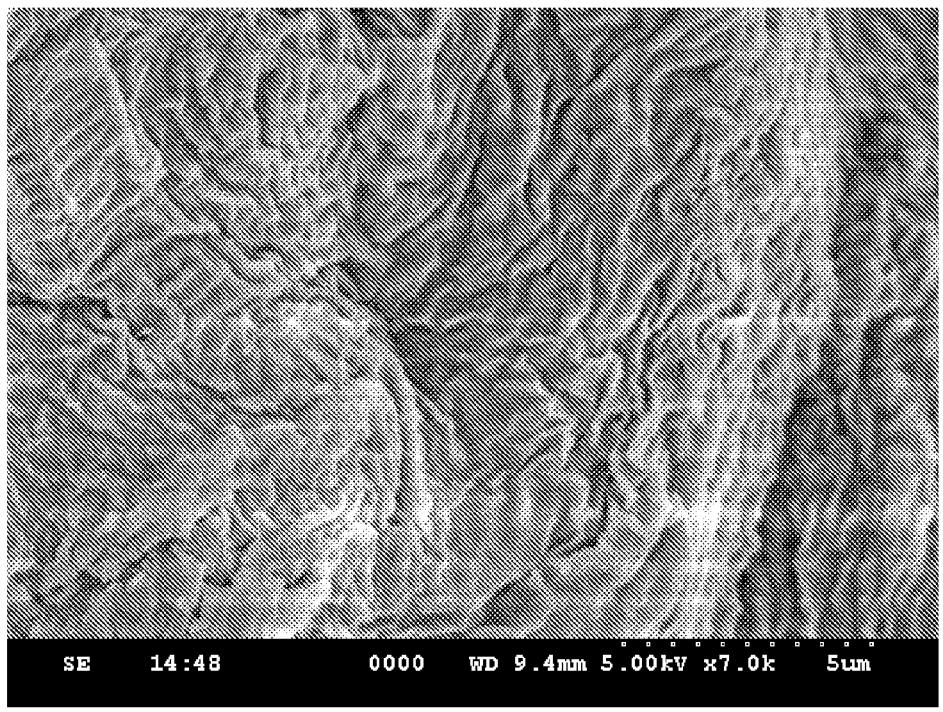
FIG. 2 illustrates a scanning electron micrograph (Magnification 7,000 times) of pristine guar borax (comparative example II).

The present description refers to a number of routinely used chemical terms. Nevertheless, definitions of selected terms are provided for clarity and consistency.

As used herein, the term "Free Swell Capacity" (FSC), also called "Total Absorption" refers to the amount (g) of fluid absorbed per gram of the composition. Typical fluids are blood, synthetic blood and saline solutions (0.9% Weight/Weight NaCl solution, hereinafter called 0.9% NaCl solution or saline).

As used herein, the term "Centrifuge Retention Capacity" (CRC) also called "Retention", refers to the amount (g) of fluid retained per gram of the composition, following exposure of the composition to a centrifugation force of 250 G. Typical fluids are blood, synthetic blood and saline solutions (0.9% Weight/Weight NaCl solution, hereinafter called 0.9% NaCl solution or saline).

As used herein, the term "Absorption Under Load" (AUL) at 0.3 PSI, 0.7 PSI or 0.9 PSI, also called "Absorption Against Pressure", refers to the amount (g) of fluid absorbed per gram of the composition. Typical fluids are blood, synthetic blood and saline solutions (0.9% Weight/Weight NaCl solution, hereinafter called 0.9% NaCl solution or saline).

As used herein, the term "rewet" or "wet-back" refers to a physical characteristic of a diaper, a sanitary napkin, an airlaid, an absorbent core or an incontinence garment, measuring the capacity of these absorbent products to retain fluids under applied pressure (0.7 PSI).

As used herein, the term "stain area" or "diffusion" refers to a physical characteristic of a diaper, a sanitary napkin, an airlaid, a C-fold, an absorbent core or an incontinence garment, measuring the staining area ($cm^2$) produced for a given amount of a liquid.

As used herein, the term "penetration time" refers to a physical characteristic of a diaper, a sanitary napkin, an airlaid, an absorbent core or an incontinence garment, measuring the time taken by an absorbent product to absorb a given amount of a liquid.

As used herein, the term "nanocomposite(s)" refers to materials comprising a nanoscale dispersion of phyllosilicates in a polymer network. Typical phyllosilicate nanocomposites are exfoliated nanocomposites, intercalated nanocomposites and semi-exfoliated nanocomposites.

As used herein, the term "phyllosilicates" or "sheet-like silicates", refers to aluminosilicates having a thickness of about 1 nm, while having a length and a width ranging from 300 to 500 nm. Phyllosilicates are a major constituent of clays. Size, composition and shape of phyllosilicates will vary depending on the clay sources. Phyllosilicates typically have the general molecular formula: $Al_2O_3.4\ SiO_2.H_2O$.

As used herein, the term "intercalated nanocomposites", also referred to as "sandwich nanocomposites", refers to nanocomposites composed of repeating and alternating phyllosilicate-polymer layers. Within theses intercalated nanocomposites, the spacing between the phyllosilicate layers is increased to provide for the insertion of a polymer.

As used herein, the term "exfoliated nanocomposites", also referred to as "phyllosilicate dispersions", refers to nanocomposites comprising delaminated phyllosilicates which are dispersed throughout a polymeric network.

As used herein, the term "semi-exfoliated nanocomposites", refers to nanocomposites comprising partially exfoliated clays. Within these semi-exfoliated nanocomposites, clays are delaminated into smaller units comprising from about 45 to 70 phyllosilicate blocks. Clays usually comprise units having from about 85 to 140 phyllosilicate blocks as defined by Chenu et al. (*Comptes Rendus de l'Académie des Sciences*, Série 2, 1990, 310 (7 série 2), PP. 975-980). Within these semi exfoliated nanocomposites, the smaller phyllosilicate units are dispersed uniformly throughout the polymer.

As used herein, the term "polysaccharide" refers to polymers comprising a backbone comprising at least 90% of monosaccharide repeating units and/or derivatized monosaccharide repeating units. Non-limiting examples include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose (representative examples include carboxyalkylated cellulose and carboxymethyl cellulose), oxidized polysaccharides, sulfated polysaccharides, cationic polysaccharides, pectin, arabic gum, karaya gum, xanthan, kappa, iota or lambda carrageenans, agar-agar and alginates. Non-limiting examples of mannose-based polysaccharides include guar gum, tara gum, locust bean gum, konjac, mesquite gum, and fenugreek extracts.

As used herein, the term "monosaccharide unit", refers to cyclic $C_5$-$C_6$ aldoses or ketoses. Non limiting examples of $C_5$-$C_6$ aldoses include allose, altrose, glucose, mannose, gulose, idose, galactose, talose, ribose, arabinose, xylose, lyxose. Non limiting examples of $C_5$-$C_6$ ketoses include ribulose, xylulose, fructose, sorbose and tagatose.

As used herein, the term "monosaccharide derivatives" refers to any chemically or enzymatically modified monosaccharide unit.

As used herein, the term biodegradable refers to any substance which is degraded to at least 50%, within 56 days or less, according to the OECD test method 302B. A specific, non-limiting example of biodegradable substances are polysaccharides.

As used herein, the term "airlaid" refers to a type of absorbent core, usually located inside sanitary napkins and baby diapers. Airlaids are fabricated using cellulose "fluff" fibers. However, they can also be manufactured using absorbent or superabsorbent materials, and/or bi-component fibers. Airlaids are generally fabricated using an air-suspension of particles and fibers which are forced to deposit on a vacuumed screen. The resulting deposit is then compressed, resulting in an airlaid.

Figure 21:
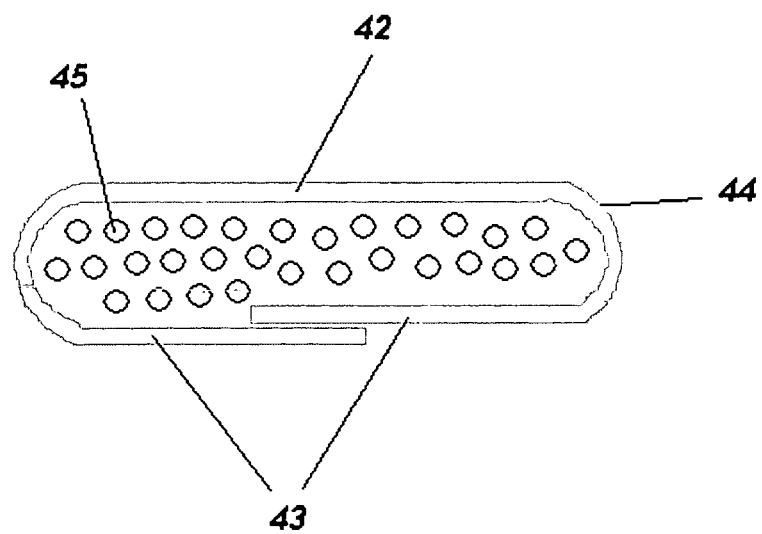
FIG. 21 illustrates a cross-sectional view of a C-fold design made from a non-woven airlaid (44); the superabsorbent (45) is placed inside the main section (42) and the two folding sections (43) are folded and glued over each other.

As used herein, the term "C-fold" refers to a type of absorbent core, usually located inside sanitary napkins, which is manufactured using an airlaid (see FIG. 21). The interior spacing of the "C-fold" usually comprises superabsorbent materials.

As used herein, the term "pristine" refers to a polysaccharides not comprising any phyllosilicate dispersions (i.e. not a nanocomposite).

As used herein, the term "residence time" refers to the time taken by a material to pass trough the extruder, from the feed port to the die. The residence time is generally measured by adding a small amount of material containing a coloring agent into the feed port. The time is started when the material containing the colorant enters the barrel and is stopped when it is observed at the die exit.

As used herein, the term "extrudate temperature" refers to the temperature of the material at the die exit as measured by a portable thermocouple plunged into one of the die openings.

As used herein, the term "ionic polysaccharides" refers to both anionic and cationic polysaccharides.

As used herein, the term "fibers" refers to both natural and synthetic fibers.

Figure 15:
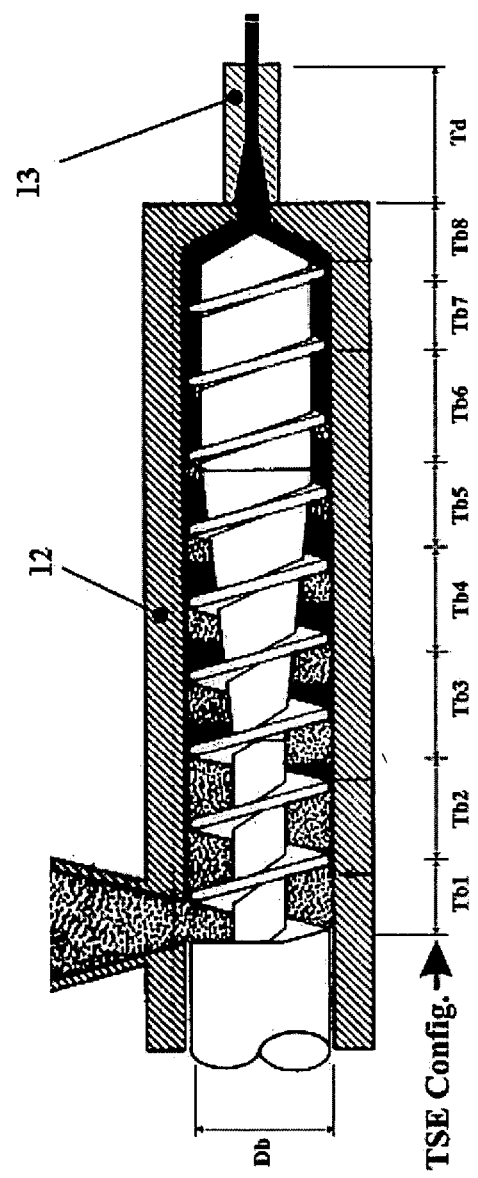
FIG. 15 illustrates a twin screw extruder (TSE) (12) including a die plate (13); the barrel diameter is illustrated as Db, and comprises heating sections Tb1, Tb2, Tb3, Tb4, Tb5, Tb6, Tb7, Tb8, and Td.

T: Extrudate temperature (° C.); Ω: Screw rotational speed, expressed in RPM (revolutions per minute); Q: Extruder throughput or flow rate (Kg/h); $Q_{die}$: Die extrusion throughput (Kg/h); $Tb_x$: Temperature (° C.) of barrel section X (FIG. 15); Td: Die temperature (° C.) (FIG. 15); HP: Motor power of the extruder (Horse Power); $D_b$: Extruder barrel diameter (mm) (FIG. 15).

AFM: Atomic Force Microscopy.

SEM: Scanning Electron Microscopy.

In a broad sense, the present invention relates to novel absorbent or superabsorbent materials. More specifically, the present invention relates to superabsorbent nanocomposite materials comprising polysaccharides and phyllosilicates. Yet more specifically, the present invention relates to superabsorbent nanocomposite materials comprising biodegradable polysaccharides and phyllosilicates. The biodegradable absorbent or superabsorbent polysaccharides may be self-entangled in a glass-like pattern and/or may be cross-linked.

The superabsorbent polysaccharide-phyllosilicate nanocomposite materials of the present invention possess distinct macromolecular patterns. Within these nanocomposite materials, the phyllosilicates are dispersed throughout the polysaccharide network following an exfoliated and/or a semi-exfoliated pattern. Is was surprisingly discovered that these patterns are influenced by both mixing (shearing forces) and process conditions involved in the preparation of the nanocomposite material.

Preferred polysaccharides are guar and starch. Guar is particularly preferred when it is cross-linked in the presence of phyllosilicates, while starch is particularly preferred when it is self entangled (forming a glass-like polysaccharide) in the presence of phyllosilicates.

Biodegradable polysaccharide-phyllosilicate superabsorbent nanocomposites are a new class of materials. Phyllosilicates constitute a major constituent of clays, an environmentally friendly and naturally abundant material. It was surprisingly discovered that polysaccharide-phyllosilicates nanocomposite materials having superabsorbent properties could be prepared by combining the biodegradability and high absorbency properties of polysaccharides with the strength and stability properties of clay. These polysaccharide-phyllosilicates nanocomposite materials were prepared using solution or extrusion methods.

Figure 3:
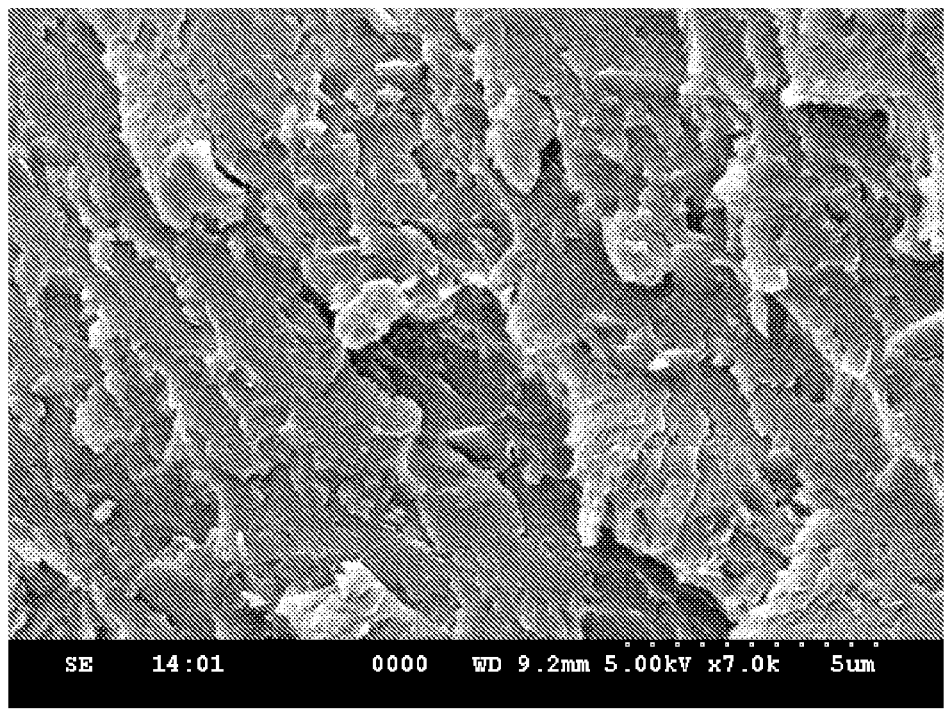
FIG. 3 illustrates a scanning electron micrograph (Magnification 7,000 times) of a 9.1% (w/w) bentonite (Bentonite Performance Minerals)—glass-like starch nanocomposite (example 1).
Figure 4:
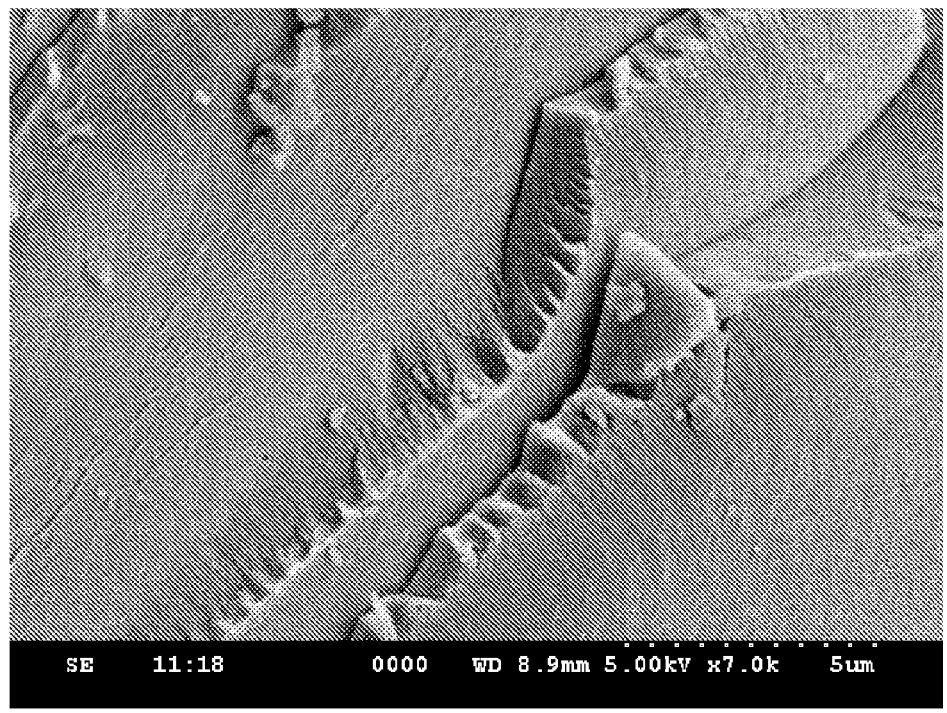
FIG. 4 illustrates a scanning electron micrograph (Magnification 7,000 times) of pristine glass-like starch (comparative example 1).
Figure 7:
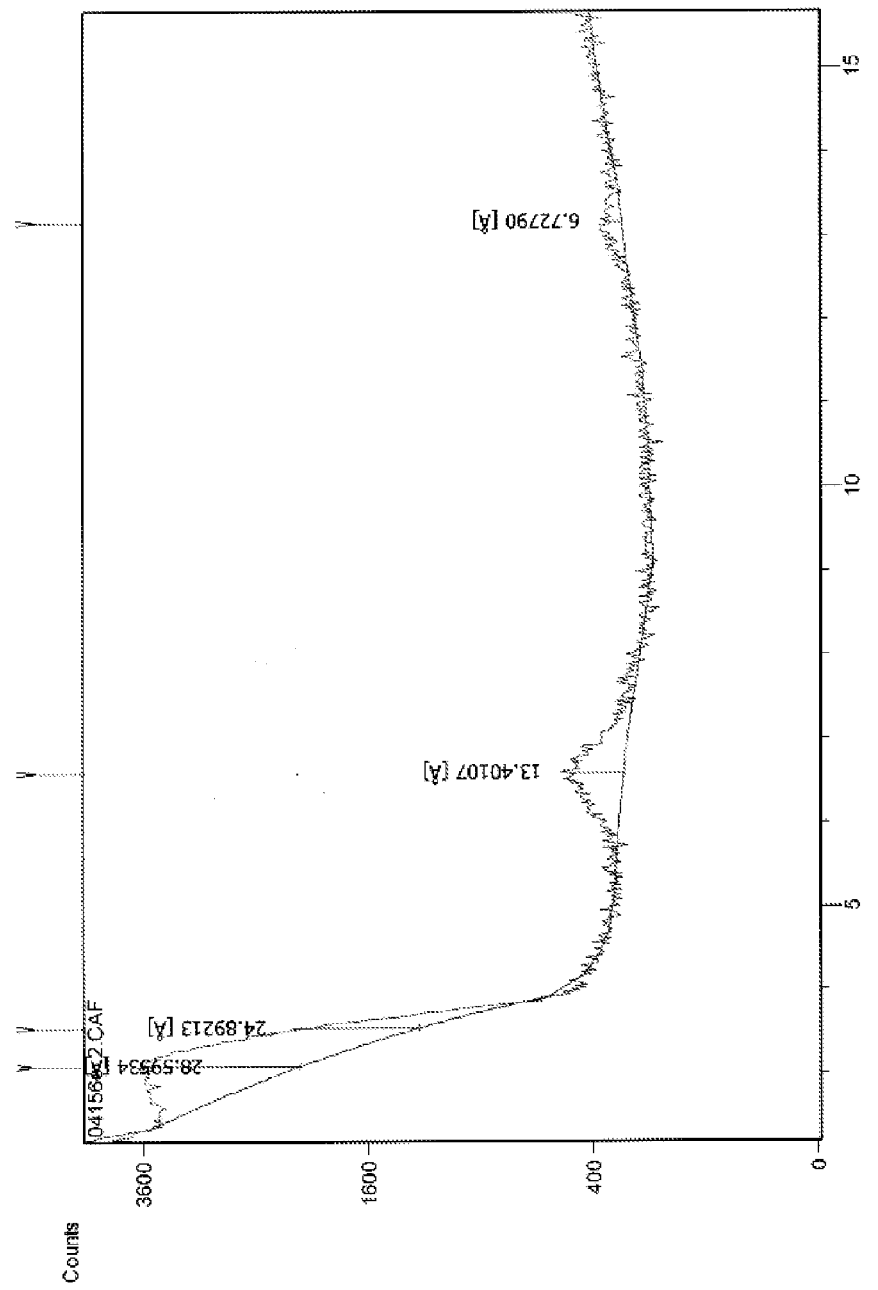
FIG. 7 illustrates an X-ray diffraction spectrum of a 9.1% (w/w) bentonite (Bentonite Performance Minerals)—glass-like starch nanocomposite (example 1).
Figure 8:
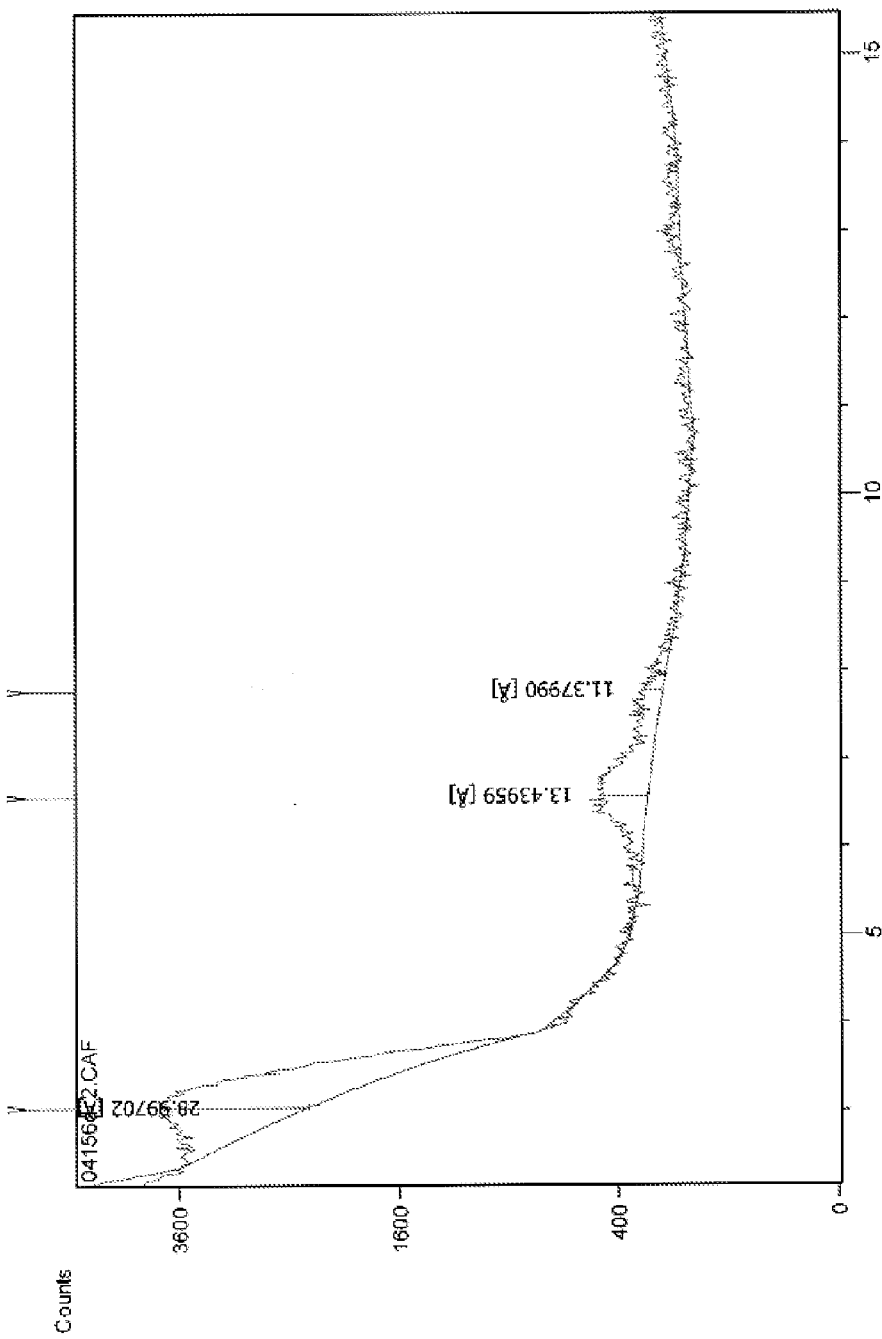
FIG. 8 illustrates an X-ray diffraction spectrum of a 23.1% (w/w) bentonite (Bentonite Performance Minerals)—glass-like starch nanocomposite (example 2).
Figure 9:
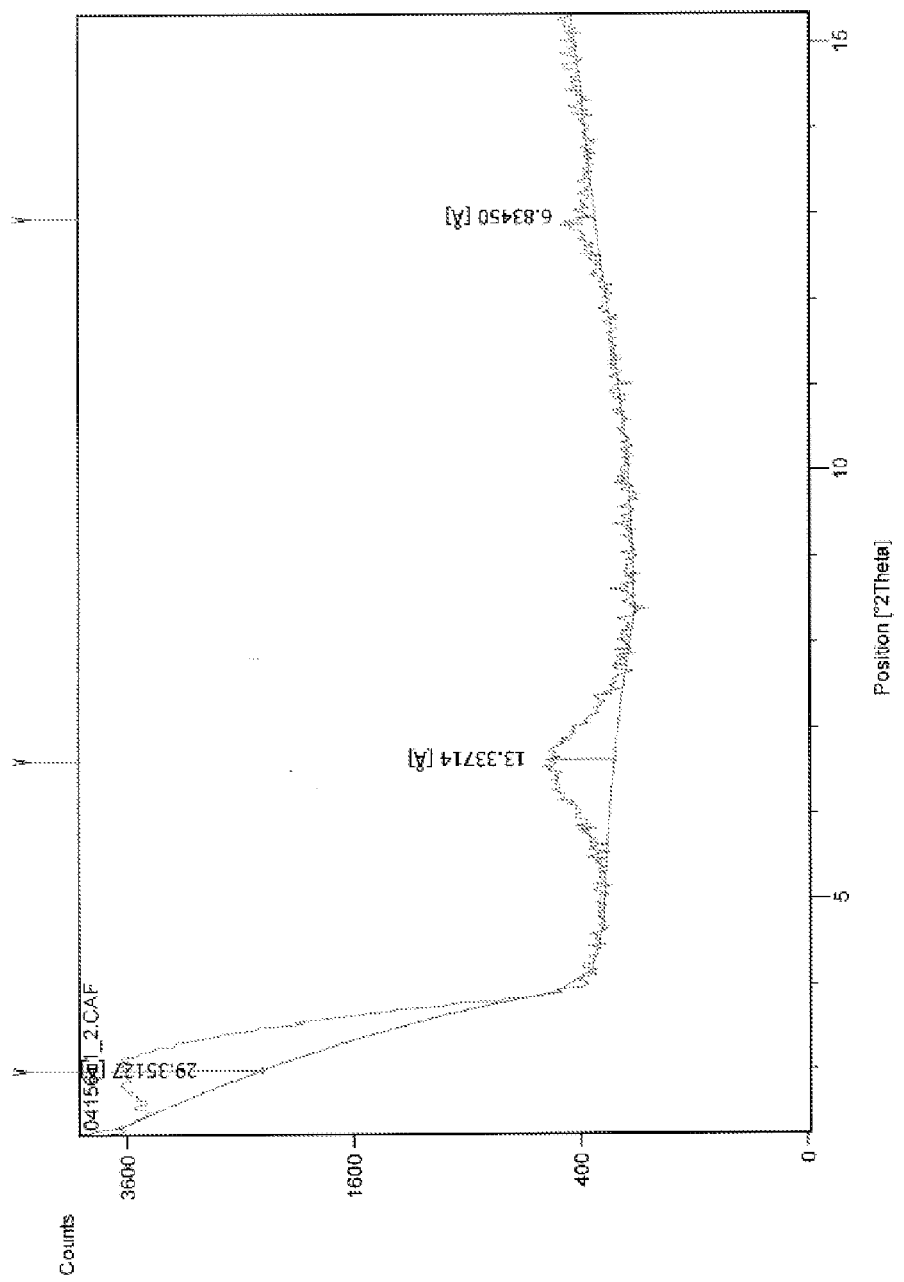
FIG. 9 illustrates an X-ray diffraction spectrum of pristine glass-like starch (comparative example I).
Figure 10:
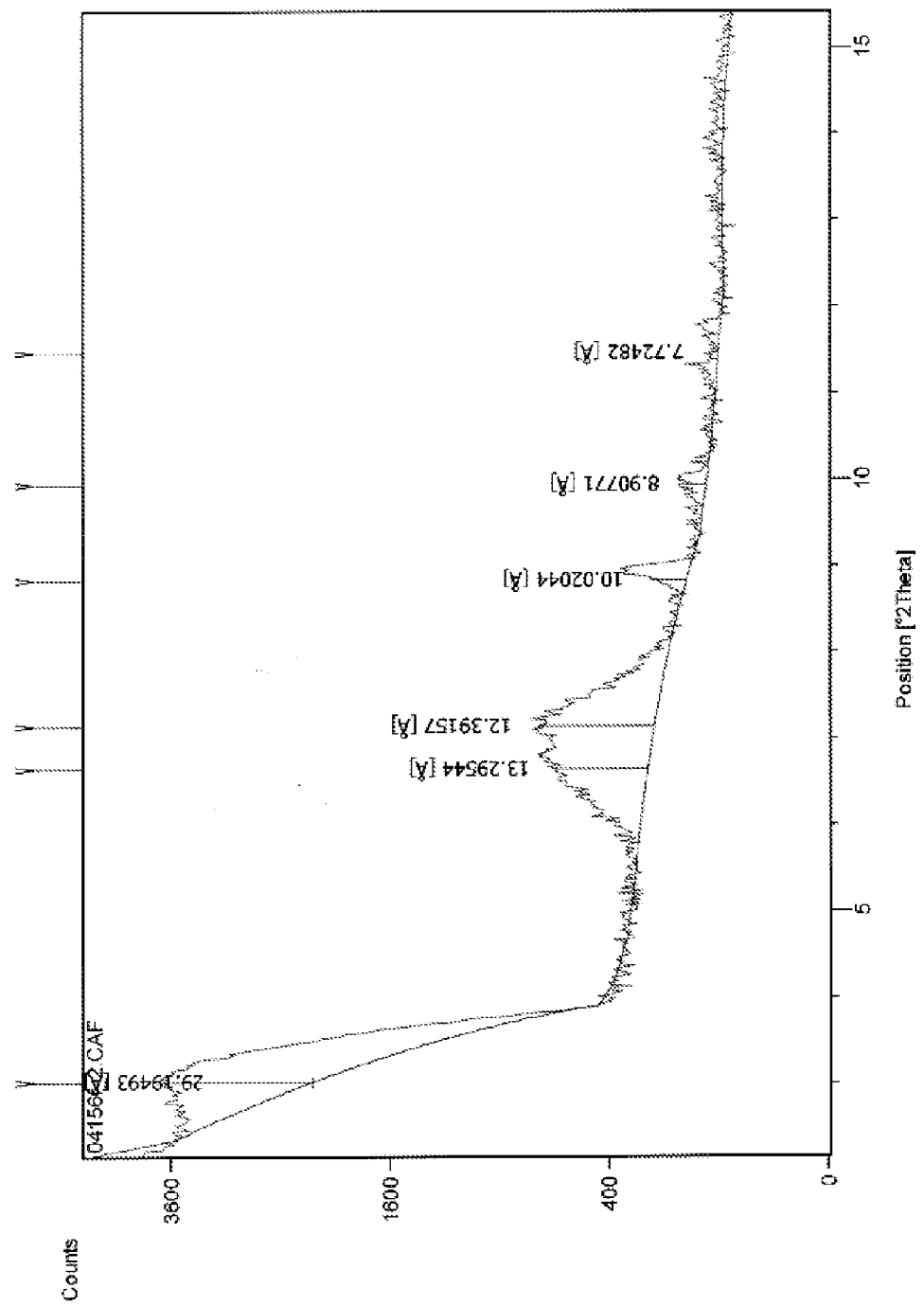
FIG. 10 illustrates an X-ray diffraction spectrum of bentonite (Bentonite Performance Minerals, LD-12 dust).

Extruded nanocomposites (Examples 1 and 2 respectively) were characterized by X-Ray diffraction (FIGS. 7 and 8 respectively). A broad shouldering could be observed at 4° Theta on both spectra. Pure glass-like starch (FIG. 9, comparative Example I) and pure bentonite (FIG. 10) do not exhibit such a broad shouldering. The shouldering is indicative of the extruded nanocomposites being characterized by an exfoliated pattern, having an interlayer spacing of about 20-25 Å. The presence of an exfoliated pattern could be confirmed by scanning electron microscopy "SEM" (FIGS. 3 and 4). A chaotic, but glass-like surface (flat surface, disrupted by small breaks) could be discerned from FIG. 3. A smoother, glass-like starch surface, could be discerned from FIG. 4.

Figure 11:
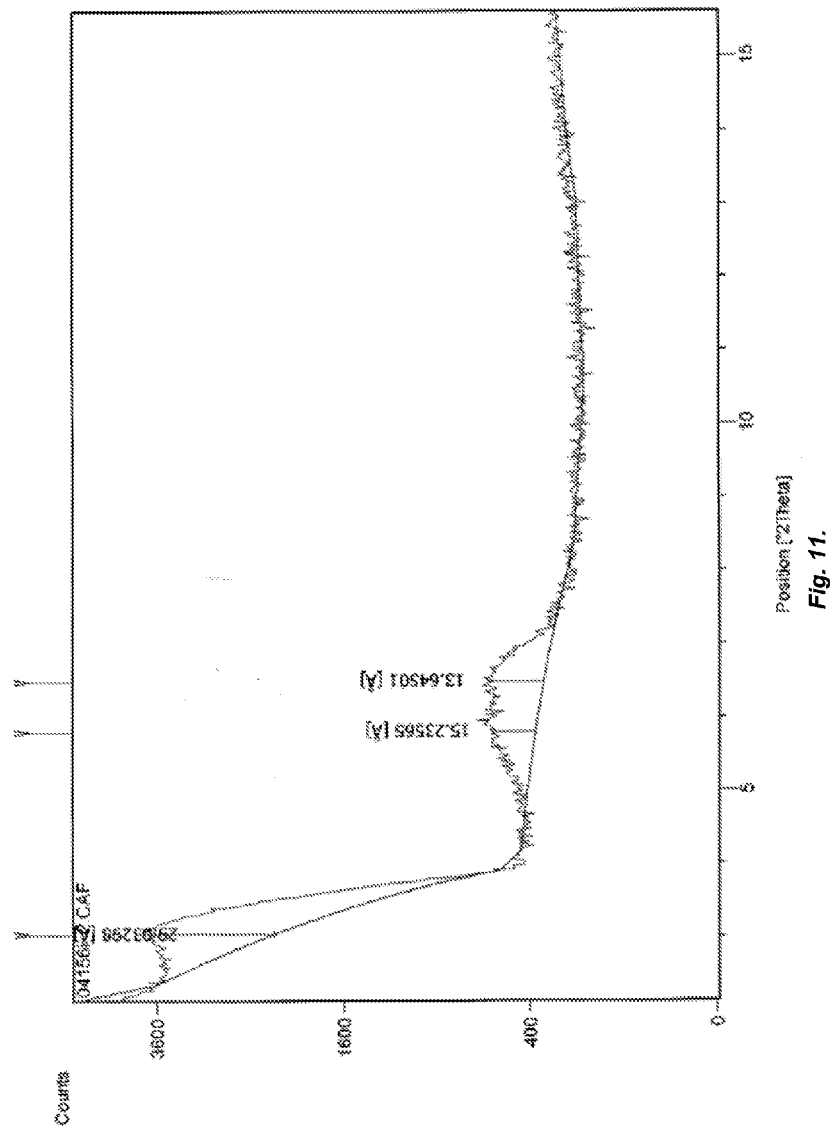
FIG. 11 illustrates an X-ray diffraction spectrum of 20% (w/w) bentonite (Minelco MB 300)—guar borax nanocomposite (example 7).
Figure 12:
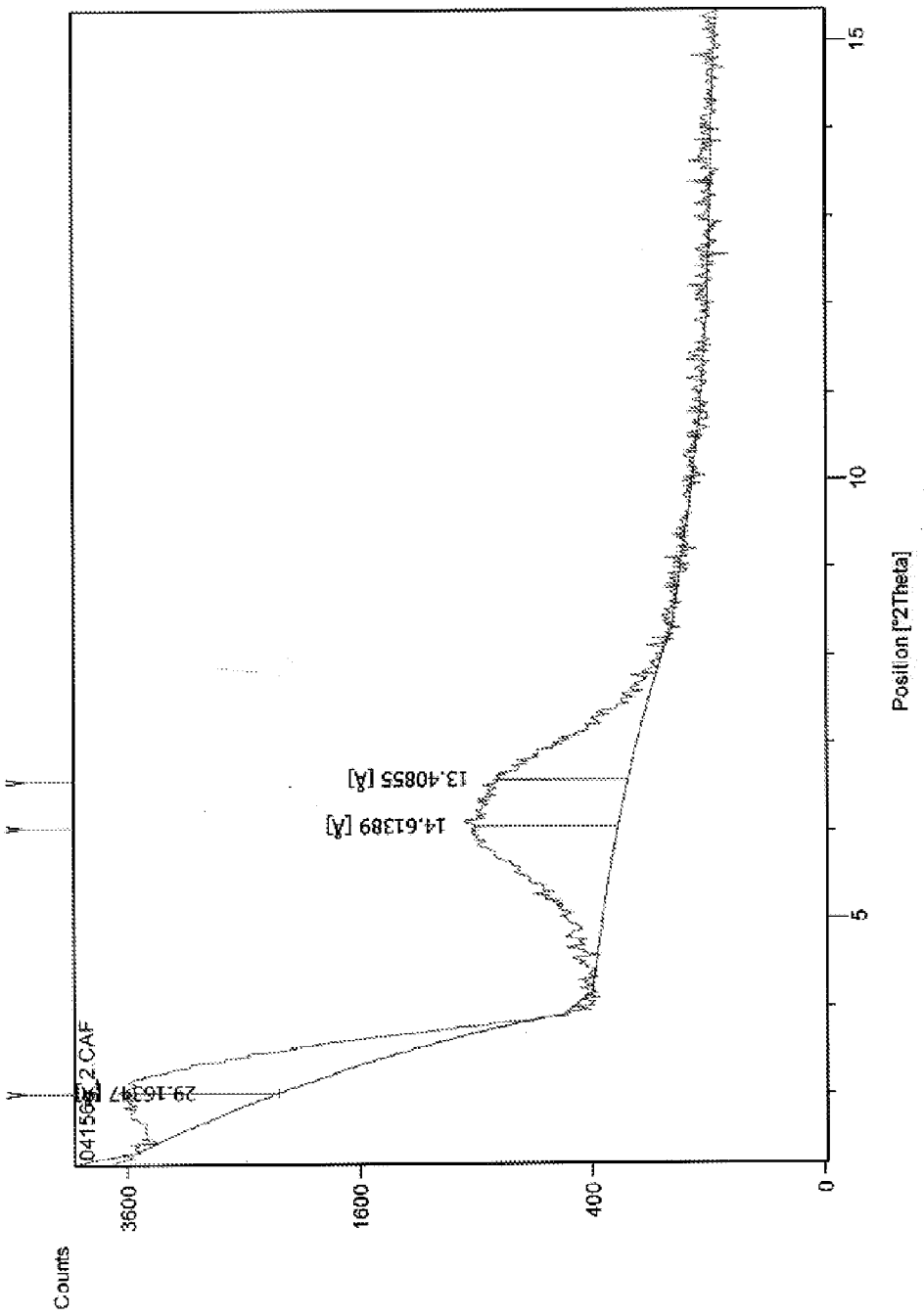
FIG. 12 illustrates an X-ray diffraction spectrum of bentonite (Minelco MB 300).
Figure 13:
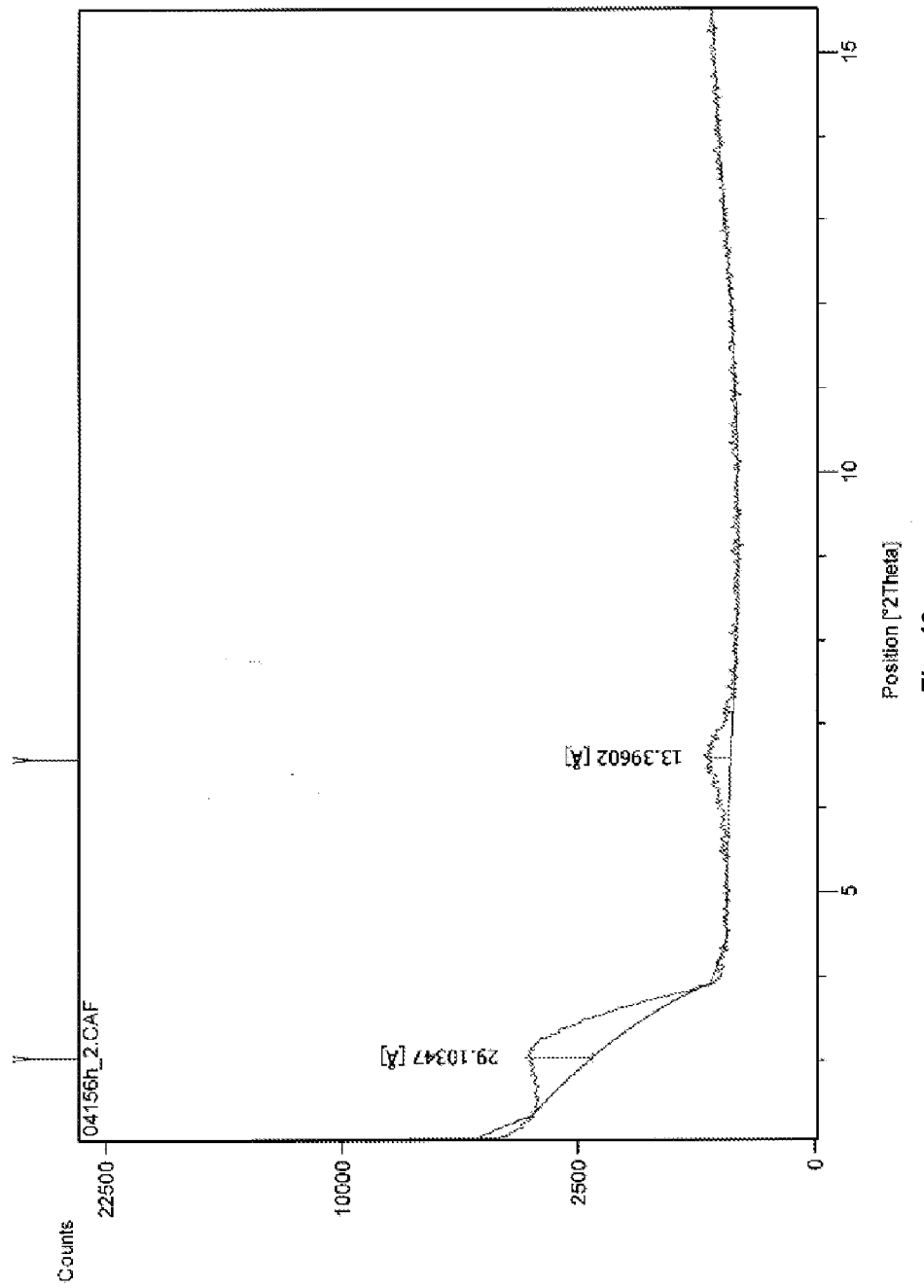
FIG. 13 illustrates an X-ray diffraction spectrum of pristine guar-borax (comparative example II).

Solution generated nanocomposites possess a different macromolecular pattern. Solution based nanocomposites (Example 7) were also characterized by X-Ray diffraction (FIG. 11). However, no shouldering effect around 3-4° Theta could be discerned. Moreover, pure guar borax (FIG. 13, comparative example II), and pure bentonite (FIG. 12), also show no shouldering. The absence of any shouldering effect is indicative that interlayer spacing between the phyllosilicates remains unchanged in solution-based nanocomposites.

Figure 5:
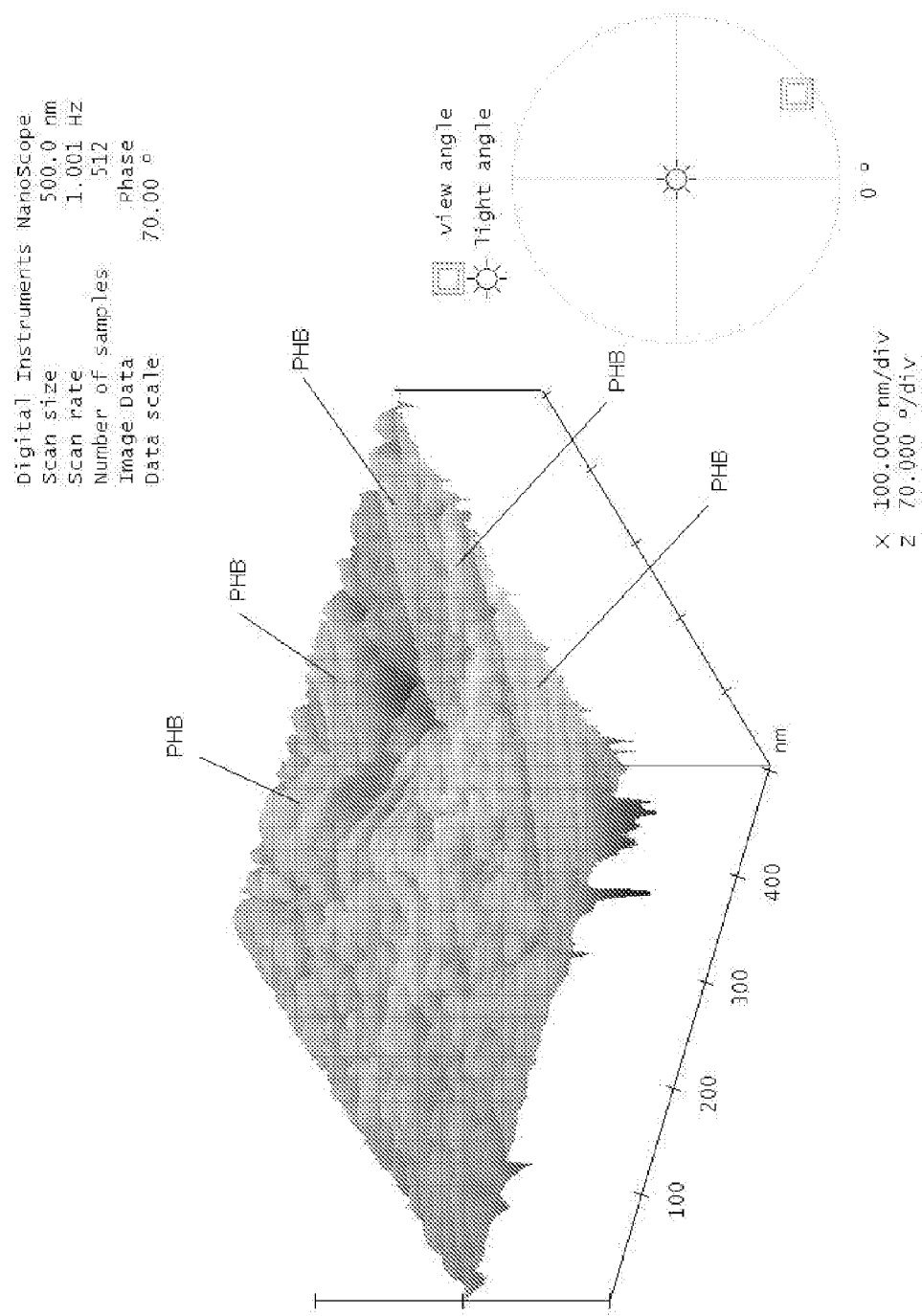
FIG. 5 illustrates an atomic force micrograph of a 20% (w/w) calcium bentonite (Minelco MB 300)—guar borax nanocomposite (example 7); phyllosilicate blocks, indicating a semi-exfoliated pattern, were marked as PHB.
Figure 6:
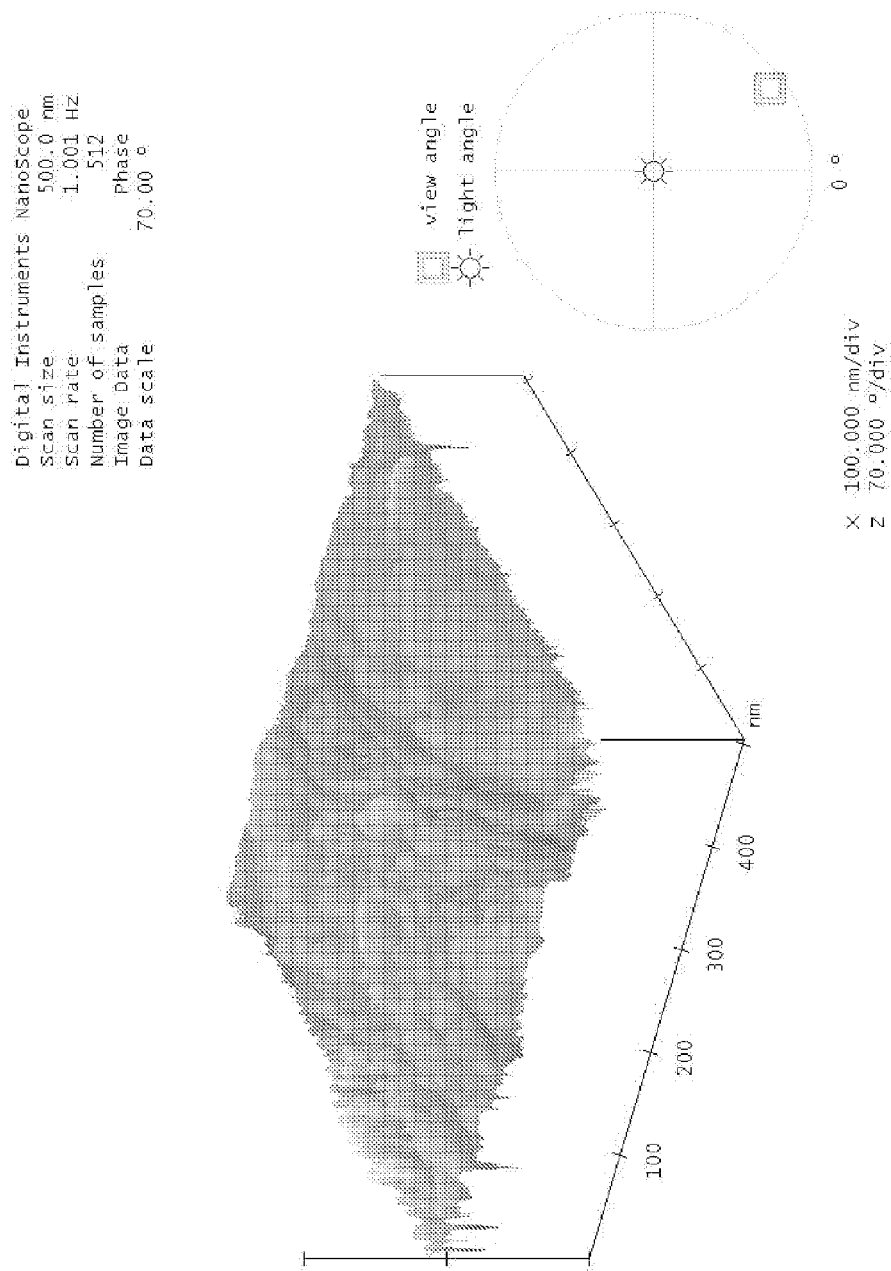
FIG. 6 illustrates an atomic force micrograph of pristine guar-borax (comparative example II).

The solution generated nanocomposites were further characterized by atomic force microscopy "AFM", which indicated the formation of a semi-exfoliated pattern. Many phyllosilicate blocks (PHB), indicative of a semi-exfoliated pattern, could be discerned on the atomic force micrograph of the 20% calcium bentonite/guar-borax nanocomposite (FIG. 5). The phyllosilicate blocks have a general thickness of about 50 nm. However, as can be discerned from FIG. 6, guar-borax comprises a smooth surface, disrupted only by long and curvy breaks in the material. The presence of a semi-exfoliated pattern could be further confirmed by scanning electron microscopy "SEM" (FIG. 1 and example 7). A chaotic surface having many small particles embedded therein could be discerned for the 20% bentonite/guar-borax nanocomposite (FIG. 1). An organized, relatively smooth surface, disrupted only by little wrinkles, could be discerned for pristine guar-borax (FIG. 6, comparative example II).

It was discovered (Examples 40 and 41) that polysaccharide-phyllosilicate nanocomposites having a particle size ranging from about 88 μm to about 590 μm, are especially useful for absorbing fluids. Furthermore, in contrast to pristine polysaccharides, these nanocomposites also exhibit performance stability over a wide range of particle sizes.

Figure 24:
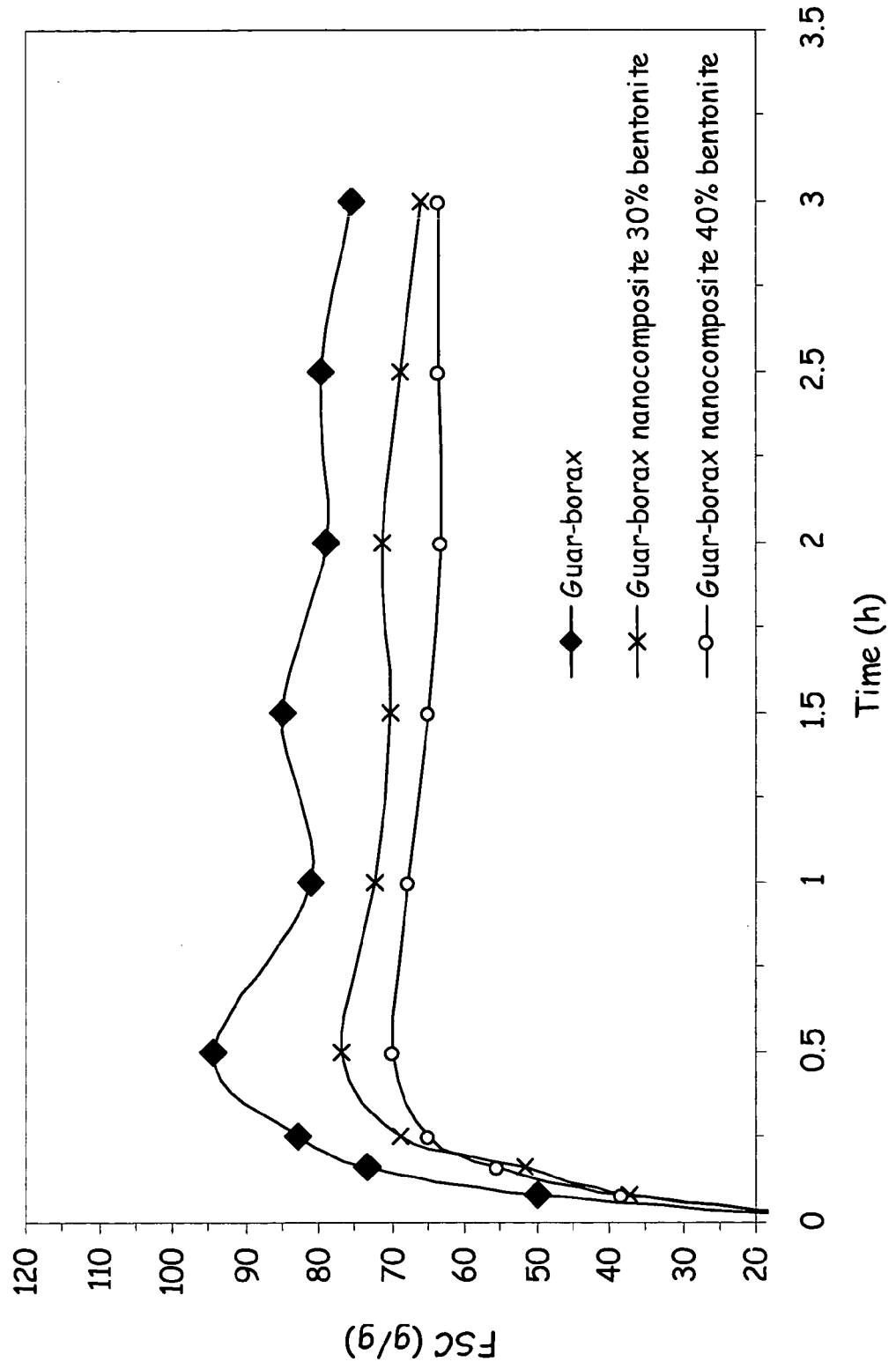
FIG. 24 illustrates the absorption kinetics of guar-borax, 30% bentonite—guar borax nanocomposite and, 40% bentonite—guar borax nanocomposite.

Moreover, in contrast to pristine polysaccharides, the polysaccharide-phyllosilicate nanocomposites of the present invention do not suffer from gel flowing or syneresis (FIG. 24). As can be observed from FIG. 24, both the polysaccharide and the nanocomposite material reach a maximum FSC value within 30 minutes of exposure. The maximum FSC value is maintained by the nanocomposite materials indicative of the absence of gel flowing and syneresis. However, in the case of the polysaccharide (Guar-borax) a drop in the FSC value can be observed indicative of gel flowing and syneresis.

The polysaccharide-phyllosilicate nanocomposites of the present invention can be used to absorb both simple and complex fluids (i.e. water, aqueous solutions, physiological solutions, saline solutions, blood, synthetic blood, serum or menstrual fluids). Indeed, it was surprisingly discovered that the polysaccharide-phyllosilicate nanocomposites of the present invention have an increased ability to absorb bovine blood, in comparison to pristine polysaccharides (polysaccharides without phyllosilicates). This has important implications, taking into consideration feminine hygiene products and wound dressings in which the absorbents have to absorb blood, synthetic blood, serum, menstrual fluids as well as physiological fluids. It is important to note that even though the polysaccharide-phyllosilicate nanocomposites of the present invention demonstrate an increased ability to absorb complex fluids, they remain effective in their ability to absorb simple fluids. These improved absorptive characteristics are illustrated in Examples 3-6 and 42-45. The 20% bentonite/guar-borax nanocomposite exhibited in most cases higher FSC and CRC values in blood or synthetic blood, in comparison to pristine polysaccharide. Furthermore, the polysaccharide-phyllosilicate nanocomposites of example 7 also exhibited a reduced penetration time in most Airlaids and C-Folds, while also reducing the staining area (blood or synthetic blood). Reduced acquisition times allow for the sanitary napkins to handle higher fluid flow rates, while smaller staining areas prevent leakages of the hygiene product.

Surprisingly, compared to the absorptive properties of the clay and the pristine polysaccharide, a synergistic effect is discerned for the polysaccharide-phyllosilicate nanocomposites of the present invention. Synergistic interactions are observed when the absorptive performances of the nanocomposite materials exceeds that of the expected theoretical value. The theoretical value is obtained via the summation of the respective contribution of each component of the nanocomposite (i.e. polysaccharide and clay), as illustrated below in Equation 1.

$$S_{nanocomposite} > (S_{clay} \times C_{clay}) + (S_{polysaccharide} \times C_{polysaccharide}) \quad \text{Equation 1}$$

In Equation 1, $S_{clay}$, $S_{polysaccharide}$, and $S_{nanocomposite}$ are the absorption performances of the clay source, the pristine polysaccharide and the nanocomposite respectively, whereas $C_{clay}$ and $C_{polysaccharide}$ are the weight fractions of the components making up the nanocomposite material.

The observed synergistic interactions are especially pronounced with exfoliated nanocomposites. The observed synergistic interactions are acceptable with semi-exfoliated nanocomposites. The synergistic interactions can be observed with both simple fluids and complex fluids (blood, menses or serum).

Low production costs, are a further advantage of the polysaccharide-phyllosilicate nanocomposites of the present invention; clay being an inexpensive and readily available material.

The superabsorbent polysaccharide-phyllosilicates nanocomposites of the present invention may be incorporated into absorbent personal hygiene products such as, for example, baby diapers, incontinence products, sanitary napkins and the like. They may be also used in absorbent members such as absorbent cores, airlaids or foamed structures.

The superabsorbent polysaccharide-phyllosilicate nanocomposites of the present invention may also be used in several other applications such as in food pads, in agricultural and forestry applications for the retention of water in the soil and for the release of water to the roots of plants and trees; in fire-fighting techniques; in bandages and surgical pads; for the cleanup of acidic or basic solution spills, including water soluble chemical spills; as polymeric gels for the controlled release of cosmetics and pharmaceuticals (also known as drug delivery systems); and in artificial snow.

The superabsorbent polysaccharide-phyllosilicate nanocomposites of the present invention may be mixed with other co-absorbent materials to provide superabsorbent compositions. In a preferred embodiment, the superabsorbent compositions comprise from about 1 to about 99% (w/w) of nanocomposite material, and from about 99 to about 1% (w/w) of co-absorbent material. Non-limiting examples of co-absorbent materials include synthetic superabsorbent polymers, mannose-based polysaccharides, ionic polysaccharides, fibers and mixtures thereof.

In a more preferred embodiment, superabsorbent compositions are prepared by mixing the polysaccharide-phyllosilicate nanocomposites with ionic polysaccharides; either cationic or anionic polysaccharides or mixtures thereof. In yet a more preferred embodiment, superabsorbent compositions are prepared by mixing the polysaccharide-phyllosilicate nanocomposites with one or more anionic polysaccharides. Non-limiting examples of anionic polysaccharides include carboxyalkyl polysaccharides, carboxymethyl cellulose, carboxymethyl starch, oxidized polysaccharides, xanthan, carrageenans, pectin and mixtures thereof. Non-limiting examples of fibers include cellulose, viscose, rayon, cellulose acetate, Nylon™, polyalkylenes, polyethylene, polypropylene, bi-component fibers, polyesters, polylactides, polypropanediols, Lyocell™, sphagnum and mixtures thereof. Non-limiting examples of mannose based polysaccharides are guar, tara, locust bean, konjac, fenugreek extracts, mesquite extracts and aloe mannans.

The synthetic superabsorbent polymers to be incorporated into the superabsorbent compositions can be generally obtained from the polymerization, preferably by radical or radical graft polymerization, of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

The superabsorbent polysaccharide-phyllosilicate nanocomposites of the present invention may be prepared following simple procedures. In one particular embodiment, an aqueous solution or suspension of a water-soluble polysaccharide is blended to homogeneity with an aqueous clay dispersion. Clays, once swollen, will delaminate under shearing conditions. It is thus critical to allow the clays to swell before the addition of the water-soluble polysaccharide solution or suspension.

Shearing rates will seriously affect the macromolecular pattern of the nanocomposite material. Low shearing rates, such as those observed with magnetic agitators, will result in the formation of a semi-exfoliated pattern. However, high shearing rates, such as those observed with extrusion or high shear mixers, will result in the formation of a more exfoliated pattern. The more exfoliated patterns are preferred for the nanocomposite materials of the present invention.

Extruders are gaining in popularity as continuous reactors for processes such as polymerization, polymer modification or compatibilization of polymer blends. An extruder was used in the preparation of glass-like absorbent starches, as described by Huppe et al. (CA 2,308,537). In the case of reactive extrusion, several organic reactions can be conducted in extruders, including polymerization, grafting, copolymer formation, molecular network formation, crosslinking, functionalization and controlled degradation (*Reactive Extrusion: Principles and Practice*, Xanthos M. Ed., Hanser Publishers, New York, 1992).

It was discovered that phyllosilicate glass-like starch nanocomposites could be produced by simply adding and mixing swollen and hydrated clays with a starch paste, followed by the extrusion of the clay-starch mixture. Once extruded, the clay-starch mixture was dried and ground. These phyllosilicate glass-like starch nanocomposites exhibit better absorbent properties than pristine glass-like starch, even though comprising a high (25%) phyllosilicate content.

Glass-like starches are composed of an amorphous network of self-entangled polysaccharide strands such as for example amylopectin and/or amylose strands. Nodes within this molecular network are simply made by hydrogen bonding. Nanocomposite absorbent materials having an amylopectin content in excess of 90% do not exhibit synergistic effects between the polysaccharide component and the phyllosilicate component.

As previously mentioned, polysaccharide-phyllosilicate nanocomposite absorbent materials can be prepared using solution methods (i.e. using an aqueous solution or an aqueous suspension of the polysaccharide). Non-limiting examples of water soluble polysaccharides include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose (examples include carboxyalkylated cellulose and carboxymethyl cellulose), oxidized polysaccharides, sulfated polysaccharides, cationic polysaccharides, pectin, arabic gum, karaya gum, xanthan, kappa, iota or lambda carrageenans, agar-agar and alginates. Particularly preferred water-soluble polysaccharides include galactomannan gums. Galactomannans are naturally occurring neutral polysaccharides consisting of a poly β-(1-4)-mannose backbone having varying degrees of substitution (DS), to which single D-galactopyranosyl residues are attached via α-(1-6) linkages.

Guar gum is derived from ground endosperm of the guar plant, which is grown extensively in the semi-arid regions of Pakistan and India. As shown below in Scheme 1, the structure of guar gum comprises a random galactose substitution ratio of 1.6:1. This ratio is subject to fluctuations from crop to crop or from subspecies to subspecies (Jasinski et al. *J. of Polym. Sci.*, part. B, 1996, 34, pp. 1477-1488).

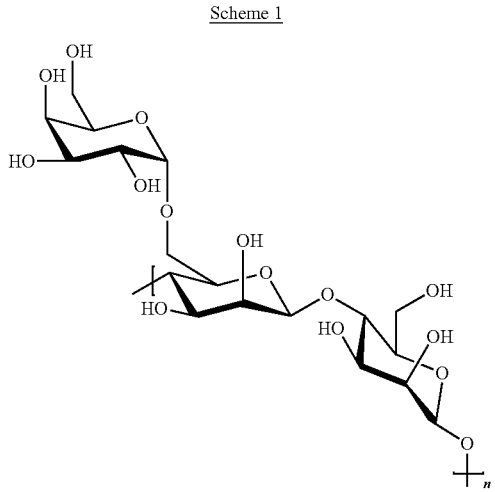

It is preferable that the polysaccharides are cross-linked when solution methods are employed to prepare the absorbent polysaccharide-phyllosilicate nanocomposite materials of the present invention. Crosslinking will prevent the polysaccharide from completely dissolving in the aqueous suspension. However, with too high a degree of crosslinking, any excess crosslinking agent will prevent subsequent swelling of the nanocomposite material, reducing its absorbent properties.

Following the mixing of a suspension of a water-soluble polysaccharide and an aqueous clay dispersion, a solution containing crosslinking agents is added to the mixture. Examples of crosslinking agents include, but are not limited to borax (for mannose polymers), boric acid (for mannose polymers), glyoxal, epichlorohydrin, sodium trimetaphosphate, sodium tripolyphosphate, phosphorous oxychloride and mixtures thereof. Additional non-limiting examples of crosslinkers known in the art include succinyl dichloride, acryloyl chloride, butanediol diglycidyl ether, ethanediol diglycidyl ether, pyromellitic dianhydride, divinylsulfones, diisocyanates, alkylene bisacrylamides and mixtures thereof. A particularly preferred crosslinking agent is boric acid or borax. This crosslinking agent is particularly useful for crosslinking galactomannans.

Sodium tetraborate (borax) and boric acid are well-documented boron derivatives for the crosslinking of cis-diols, particularly for the crosslinking of guar gum (Muller U.S. Pat. No. 4,624,868 and U.S. Pat. No. 4,333,461). Rigidifying the macromolecular architecture of guar gum using these crosslinkers, improves its gel strength in addition to improving its absorption and retention capabilities.

Borax (sodium tetraborate) and boric acid react with guar gum via borate ions in aqueous basic solutions (Pezron E. et al. *Macromolecules*, 1988, 21, 1121-1125). As shown below in Scheme 2, an aqueous solution of borax consists of a system wherein borax, borate ion and boric acid are in equilibrium. $^{11}$B NMR studies of a guar-borate derivative, illustrated the presence of a 2:1 complex of a five-membered mannosyl-borate ring and a six-membered galactosyl-borate ring (Jasinski R. et al., *J. Polym. Sc. Part B-Polym. Phys.*, 1996, 34, 1477-1488).

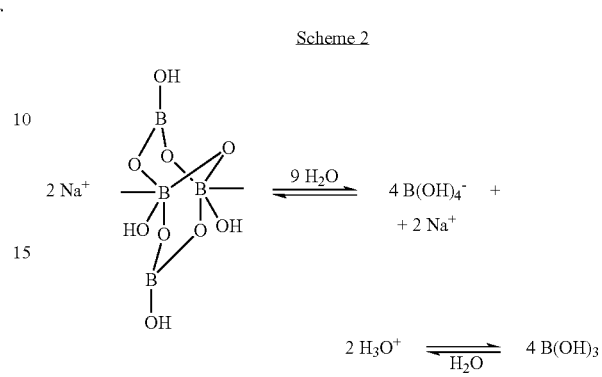

After the addition of the crosslinking agent, the combined components are left for a period of time sufficient to permit gelling. Under optimal conditions of concentration, and in absence of inhibitors, typical gelling periods are not more than about 30 minutes. The mixture at this point is quite thick and requires further processing. In order to achieve the desired consistency, the gelled product is precipitated in an excess of alcohol. Other precipitation or drying techniques can also be used.

The incorporation of a precipitation step, using an alcohol such for example methanol, ethanol, or isopropanol is preferred. The alcohol precipitation step will also remove impurities from the superabsorbent polysaccharide-phyllosilicate nanocomposite material. Moreover, a pH adjustment will improve the texture of the obtained superabsorbent polysaccharide-phyllosilicate nanocomposite material, as well as improving its aseptic properties. The product is thereafter removed by filtration, and homogenized by grinding or milling to a particle size consistent with a powdery texture. The nanocomposite product can then be further processed, depending on its intended end use.

The clay to be used in the manufacture of the superabsorbent polysaccharide-phyllosilicate nanocomposite materials of the present invention can be any clay capable of exfoliating or semi-exfoliating in aqueous solutions. The clay source can be either natural or synthetic. Examples of clays include, but are not limited to smectites, hectorites, bentonites, montmorillonites, Laponites™, celites, illites and mixtures thereof. A particularly preferred clay is bentonite, which is a montmorillonite type clay. Bentonite is essentially made from colloidal hydrated aluminum phyllosilicates and contains varying amounts of iron, alkali, and alkaline earth metals. Calcium, sodium, potassium and magnesium bentonites are preferred. Ion-exchanged benionites can also be used in the preparation of the superabsorbent polysaccharide-phyllosilicate nanocomposite materials of the present invention.

More effective superabsorbent polysaccharide-phyllosilicate nanocomposite materials are obtained when the contribution of clay component is in the range of from about 1% (w/w) to about 40% (w/w). Polysaccharide-phyllosilicate nanocomposite materials having a clay content ranging from about 1 to about 25% are especially preferred.

The polysaccharide-phyllosilicate nanocomposite materials of the present invention will now be further described as illustrated in Examples 1 to 45.

Biodegradability

Pristine polysaccharides, used to manufacture the polysaccharide-phyllosilicate nanocomposite materials of the present invention, should be absorbent and biodegradable. The biodegradability of a pristine polysaccharide was confirmed if at least 50% of the "Dissolved Organic Carbon" (DOC) content disappeared over a period of 56 days.

A glass-like starch was dispersed at a concentration of 250 mg/L, as measured by DOC. Inoculum (0.2 g/L, Activated mud, Valcartier, Canada) was added to the sample and the pH of the solution maintained between 6.5 and 8. The solution was agitated at a 175 rpm and incubated at 20° C. for 56 days. The DOC content was measured at: t=0 (prior to the addition of inoculum), t=3 h, t=14 days, t=28 days, t=42 days and t=56 days. It was observed that 92.5% of the glass-like starch was biodegraded following 14 days of exposure to the inoculum.

A guar borate was dispersed at a concentration of 250 mg/L, as measured by DOC. Inoculum (0.2 g/L, Activated mud, Valcartier, Canada) was added to the sample and the pH of the solution maintained between 6.5 and 8. The solution was agitated at a 175 rpm and incubated at 20° C. for 56 days. The DOC content was measured at: t=0 (prior to the addition of inoculum), t=3 h, t=14 days, t=28 days, t=42 days and t=56 days. It was observed that 86.7% of the guar borate was biodegraded following 14 days of exposure to the inoculum.

Blood Testing

Blood testing was done with bovine blood and with synthetic blood. Synthetic blood was prepared as follows:

To a 2 L weighted beaker, 700 mL of deionized water was added, followed by the addition of sodium carboxymethyl cellulose (14 g; DS: 0.7; MW: 90 KDa). Upon complete dissolution of the cellulose, albumin (20 g; Sigma A5253) and one pouch (15.6 g) of D-MEM/F-12 (Dulbecco's modified eagle medium, 15 mM, Hepes #12400024, Gibco-Invitrogen Corp.) were added followed by stirring until complete dissolution. $NaHCO_3$ (1.2 g) and hemoglobulin (1.75 g, from bovine blood, Sigma H2625) were then added to the solution and stirred until complete dissolution. If necessary, the pH of the solution was adjusted to 7.2 using either NaOH (1N) or HCl (1N). Finally, additional deionized water was added until the total weight of the solution reached 1000 g. The solution was allowed to stand for about 30 minutes and was then filtered (4-ply cheese cotton). The filtered solution was kept refrigerated and discarded after 10 days.

Absorbent Core Manufacture

Figure 14:
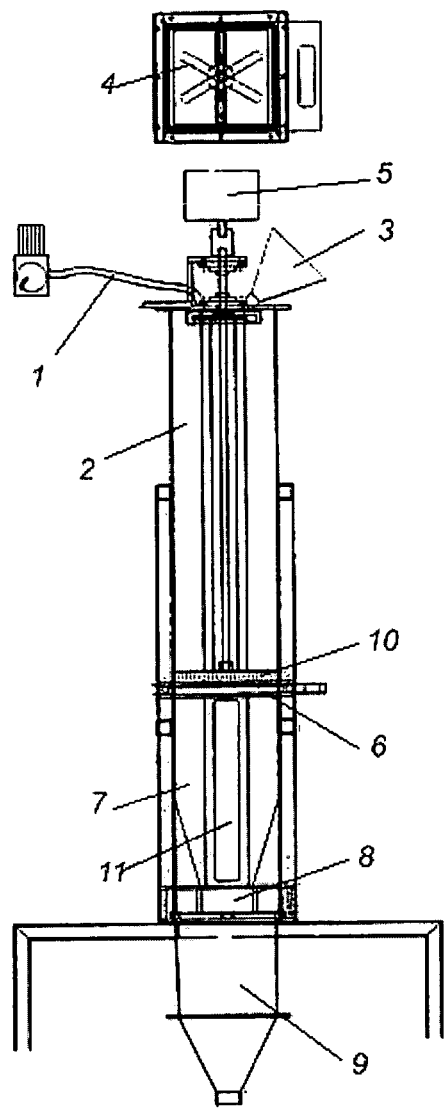
FIG. 14 illustrates an absorbent-core forming apparatus within which fluff pulp and superabsorbent particles are conveyed and deposited on a thermo-bonded non-woven filter, using a high velocity air stream. The absorbent-core forming apparatus uses compressed air (790 KPa), delivered by a compressor which is connected to the apparatus via a flexible hose (1). A pressurized air regulator is connected to the compressor. Fluff pulp and absorbent or superabsorbent materials are introduced into the mixing chamber (2) of the absorbent-core forming apparatus via a funnel (3). The fluff pulp and absorbent or superabsorbent materials are thoroughly mixed in the mixing chamber using a 6-blade propeller (4) connected to an electric motor (5). The propeller is located 59.4 mm above a 4-Mesh screen (6). A brush (10) is positioned above the screen; the brush rubbing against the screen. Particles small enough to pass through the screen are then transported to a second mixing chamber (7) via an air current, from which they are conveyed to a particle-forming cell (8) (illustrated in greater detail in FIG. 20). An air vacuum chamber (9) is located underneath the particle-forming cell. The vacuum chamber is connected to a vacuum cleaner. The core-forming process can be observed through a visualization window (11).
Figure 20:
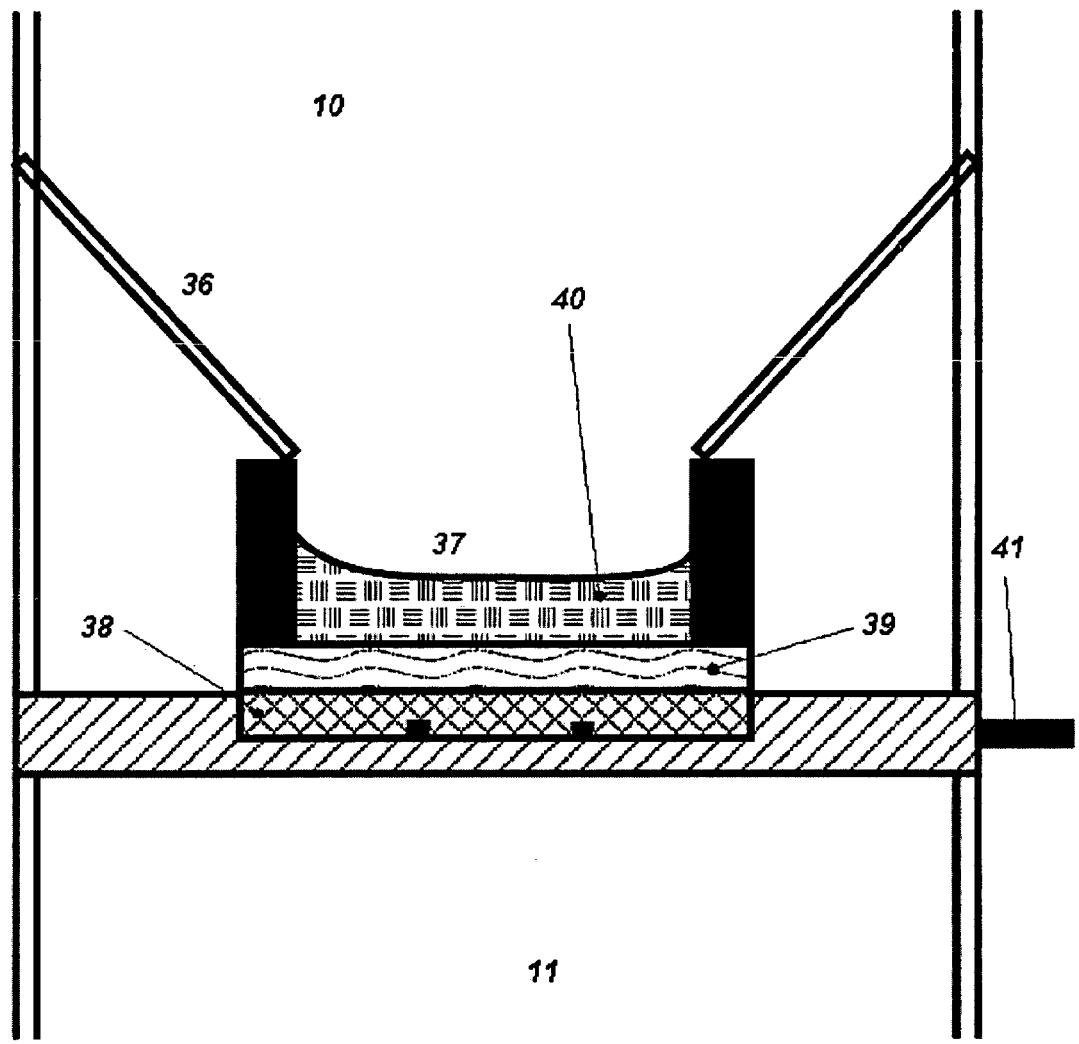
FIG. 20 illustrates a cross-sectional view of the superabsorbent particle-forming cell; a funnel (36) is positioned over a molding cell (37) in which an absorbent core (40) is produced; at the bottom of the molding cell is located a 20-Mesh screen (38); the screen is positioned below a Dounor® 23 GSM (grams per square meter) polypropylene thermobonded non-woven filter (39), retaining fine fluff and absorbent particles in the molding cell (37); air passing through the molding cell is conveyed to a vacuum chamber (11) connected to a vacuum; upon completing the formation of the absorbent core, the molding cell (37) was removed by a handled plate (41).

Absorbent cores were prepared by a process involving an absorbent core forming apparatus (see FIGS. 14 and 20).

Airlaids were manufactured by uniformly dispersing fluff pulp (0.5 g; SCA, Drummondville, Canada) on a polypropylene thermo-bonded non-woven filter (39) (FIG. 20). A molding cell (6×20 cm) (37) (FIG. 20) was assembled and positioned in the absorbent core forming apparatus. Following the creation of a vacuum in the vacuum chamber (11) (FIG. 14), the motor was switched on. The pressurized air regulator (1) (FIG. 14) was then activated allowing depressurized air to enter the apparatus. Fluff pulp (0.5 g) was then added to the absorbent core forming apparatus via a funnel (4) (FIG. 14), followed by the addition of the absorbent or superabsorbent material (1 g) and by the addition of another portion of fluff pulp (2 g). The materials were allowed to deposit in the molding cell producing an absorbent core (40) (FIG. 20). The molding cell was then slowly removed from the absorbent core forming apparatus. The obtained absorbent core (40) and the non-woven filter (39) were compressed under a pressure ranging from 1 to 3 tons, producing an absorbent core having a thickness ranging from about 3 to about 3.5 mm. The non-woven filter (39) was then removed from the compressed core providing an airlaid having a density of about 300 grams per square meter (GSM) and a superabsorbent charge of about 25%.

Simulated diapers were manufactured by uniformly dispersing fluff pulp (1.5 g; SCA, Drummondville, Canada) on a polypropylene thermo-bonded non-woven filter (39) (FIG. 20). A molding cell (10×20 cm) (37) (FIG. 20) was assembled and positioned in the absorbent core forming apparatus. Following the creation of a vacuum in the vacuum chamber (11) (FIG. 14), the motor was switched on. The pressurized air regulator (1) (FIG. 14) was then activated allowing depressurized air to enter the apparatus. Fluff pulp (2.39 g) was then added to the absorbent core forming apparatus via a funnel (4) (FIG. 14), followed by the addition of the absorbent or superabsorbent material (1.79 g). An additional portion of fluff pulp (2.39 g) and absorbent or superabsorbent material (1.79 g) was then added successively two more times. The materials were allowed to deposit in the molding cell producing an absorbent core (40) (FIG. 20). The molding cell was then slowly removed from the absorbent core forming apparatus. The obtained absorbent core (40) and the non-woven filter (39) were compressed under a pressure ranging from 1 to 3 tons, producing an absorbent core having a thickness ranging from about 4.22 to about 4.45 mm. The compressed core had a density of about 0.17 grams per square centimeter and a superabsorbent charge of about 38%. A BBA® 15 GSM spun bond non-woven material was then positioned over the compressed absorbent core, more specifically over the polypropylene thermo-bonded non-woven material, simulating a diaper top-sheet.

C-Fold Formation

An airlaid (44) (14×20 cm, 100 GSM, Thurso, Canada) was folded into a C-shape (FIG. 21). The airlaid was folded such that the main section (42) measured 6 cm and the folding sections (43) measured 7 cm. Absorbent or superabsorbent material (45) was then sprinkled inside the main section. The folding sections were then folded over the absorbent material and glued.

EXPERIMENTAL

Materials

Grade A wheat starch was obtained from Archer Daniels Midland® (Decatur, USA). Guar split and guar gums were purchased from TIC-Gum® (Belcamp, USA) and Polypro (Minneapolis, USA). White calcium bentonite (Minelco® MB 300) was obtained from Minelco Minerals® (Flixborough, UK). Gray bentonites were purchased from Aldrich® (St-Louis, USA) and Bentonite Performance Minerals® (Denver, USA, LD-12). Celite was purchased from Aldrich® (St-Louis, USA). Laponite™ and illite were purchased from the Source Clay Repository (Purdue University, West-Lafayette, USA). Research grade methanol, sodium hydroxide, and hydrochloric acid were obtained from Laboratoire MAT® (Beauport, Canada). Boric acid, borax, trisodium trimetaphosphate, sodium tripolyphosphate, and phosphorous oxychloride were all obtained from Aldrich® (St-Louis, USA). Fluff pulp was obtained from SCA® (Drummondville, Canada). Airlaids, for C-fold formation, was supplied by Concert (Thurso, Canada) BBA® 15 GSM spun bond non-woven materials, used in the manufacture of the simulated diapers, were purchased from BBA Nonwovens (Nashville, USA). The Dounor® 23 GSM polypropylene thermo-bonded non-woven material was purchased from Dounor (Neuville en Ferrain, France).

Extruder

A co-rotating intermeshing twin screw extruder (TSE) was used (Table 1). The screw design for the TSE configuration is illustrated below in Table 2.

TABLE 1

Twin screw extruders.

Figure 17:
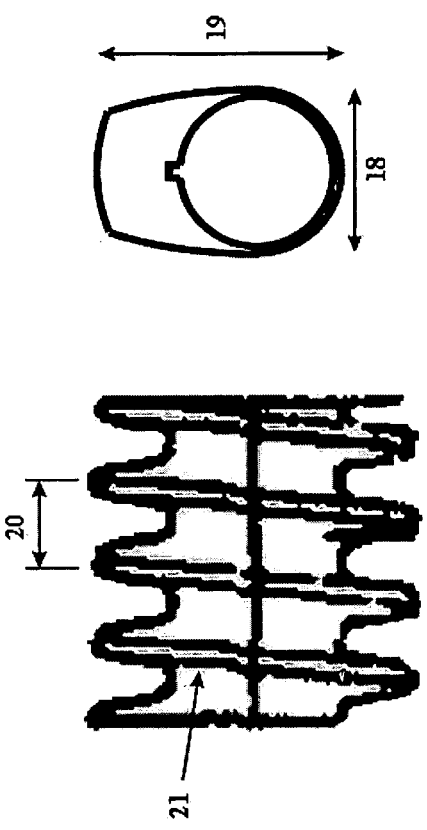
FIG. 17 illustrates an embodiment of a single lead screw element as used in the TSE; in this embodiment, the single lead screw pitch (20) was 12.7 mm, the flight width (21) was 2.7 mm, and the inner (18) and outer (19) diameters were 27.7 mm and 38.3 mm respectively.
Figure 18:
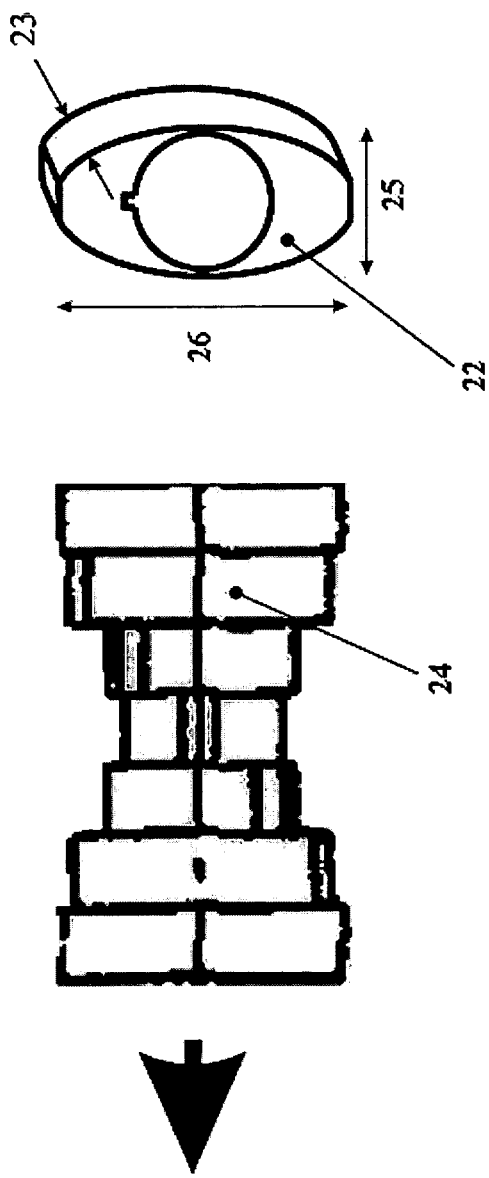
FIG. 18 illustrates a paddle block element (24) as used in the TSE, and including seven single block elements having a forward staggering angle of 30°; in this embodiment a single paddle block element (22) had a width (23) of 12.7 mm, the inner (25) and outer diameters (26) were 27.7 mm and 48.9 mm respectively.
Figure 19:
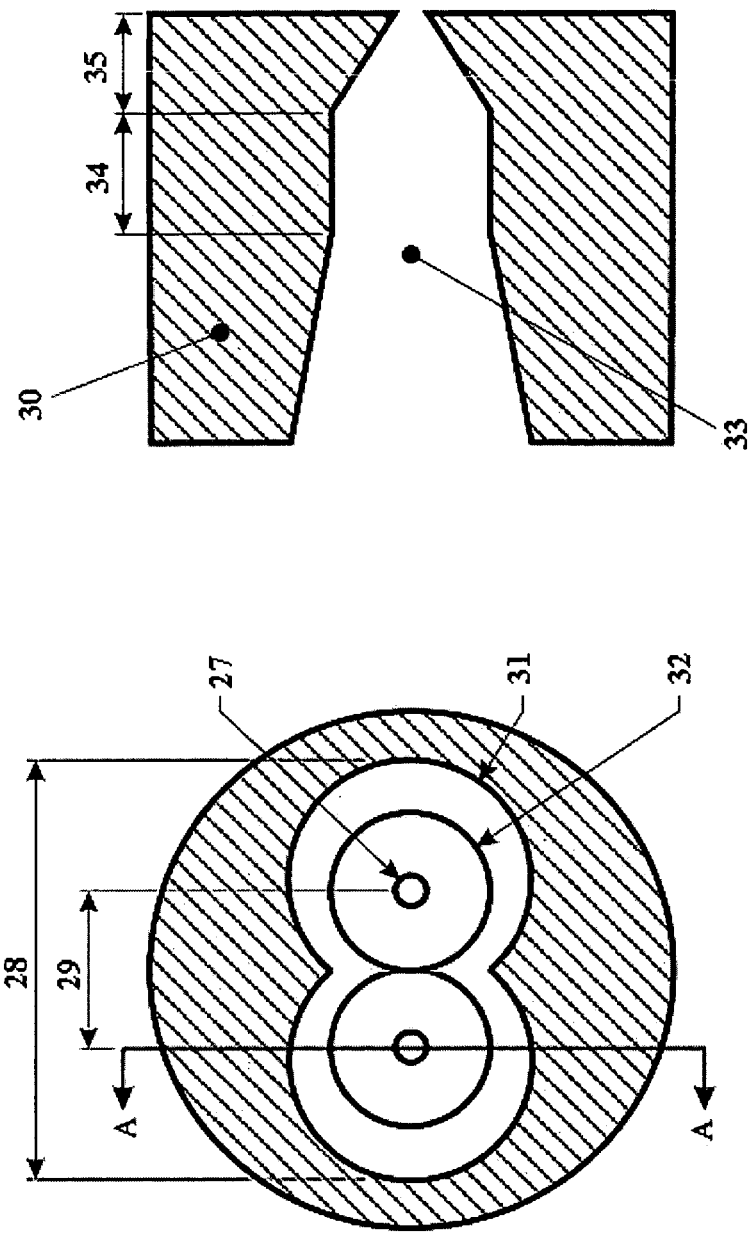
FIG. 19 illustrates an embodiment of the geometry as well as the die cross-section (30) (along the line A-A) as used in the TSE; in this embodiment, the die had two openings (27) of 6 mm (diameter) respectively, the spacing (29) between the die openings was 30 mm, the uttermost spacing (28) between the screw barrels was 89 mm, the barrel diameter (31) was 50 mm, the length of the cylindrical portion of the die (34) was 38 mm and its diameter (32) was 30 mm, the length of conical transition (35) from the cylindrical portion to the die opening was 20 mm, and the total extrudate volume (33) of the die was 250 cm$^3$.

| Manu-facturer | Machine Code | $D_b$ | HP | Barrel & Screw design | Die design |
|---|---|---|---|---|---|
| Baker Perkins Food Machinery Division | MPF-50D | 50 | 25 | FIGS. 15 to 18 & Table 2 | FIG. 19 |

TABLE 2

Screw design for the TSE configuration.
Twin Screw Design

Figure 16:
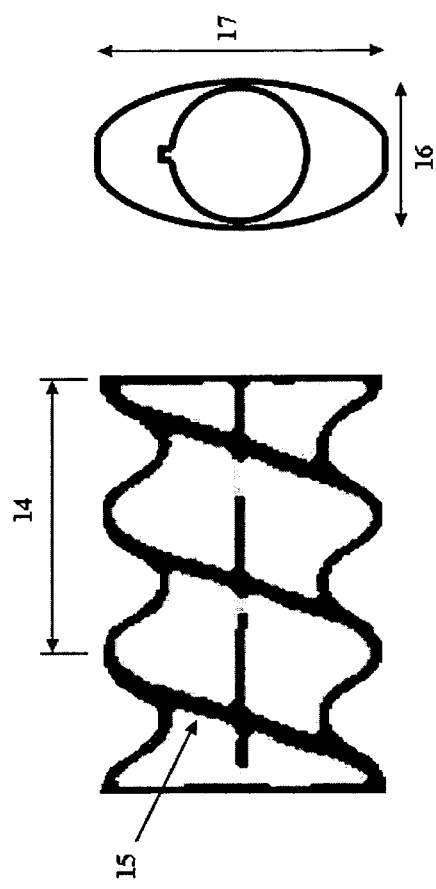
FIG. 16 illustrates an embodiment of a twin lead feed screw element as used in the TSE; in this embodiment, the twin lead feed screw pitch (14) was 50.8 mm, the flight width (15) was 1.5 mm, and the inner (16) and outer (17) diameters were 27.7 and 48.9 mm respectively.

| Feedport | Type of element | Description | Number of elements |
|---|---|---|---|
| | Twin lead feed screw | FIG. 16 | 4⅔ |
| | Single lead screw | FIG. 17 | 2 |
| | Paddle blocks | FIG. 18 | 21 (30° forward staggering angle) |
| | Single lead screw | FIG. 17 | 5½ |

Grinder

A Braun™ model KSM coffee grinder was used to grind the produced extrudate samples.

Siever

When indicated, samples were sieved using a Tyler Rota-Tap™ test sieve shaker.

Test Methods

As discussed in Modern Superabsorbent Polymer Technology (Buchholz F. L. and Graham A. T. Eds., Wiley-VCH, New York, 1998, section 4.6.1. Swelling Capacity: Theory and Practice, p. 147), several methods of measurement are used in order to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to compare the swelling capacities of the obtained absorbent products.

AUL Measurements

The Absorption Under Load (AUL) in a 0.9% NaCl solution at 0.3 PSI, 0.7 PSI and 0.9 PSI was determined according to the recommended test method 442.2-02 from EDANA, using 0.1 or 0.9 grams of the absorbent material in the apparatus.

Tea Bags for FSC and CRC Measurements

Tea bags (10×10 cm) were made from heat sealable Ahlstrom™ filter paper (16.5±0.5) g/m².

FSC Measurements

The Free Swell Capacity (FSC) in a 0.9% NaCl solution was determined according to the recommended test method 440.2-02 from EDANA. (Free Swell Capacity No. 440.2-02, Recommended test Method: Superabsorbent materials-Polyacrylate superabsorbent powders-Free Swell Capacity in Saline by Gravimetric Determination, 2002).

CRC Measurements

The Centrifuge Retention Capacity (CRC) in a 0.9% NaCl solution was determined according to the recommended test method 441.2-02 from EDANA. (Centrifuge Retention Capacity No. 441.2-02, Recommended Test Method: Superabsorbent materials-Polyacrylate superabsorbent powders-Determination of Fluid Retention Capacity in Saline Solution After Centrifugation, 2002).

Rewet

The rewet characteristic for simulated diapers, C-folds and airlaids was determined using the following method:

Natural blood (7 mL), synthetic blood (7 mL) or a 0.9% aqueous NaCl solution (55 mL), was poured onto the surface of an airlaid, a C-Fold, or a simulated diaper. The wet surface was then covered with weighted filter papers (about 8 g for C-folds and airlaids, and about 15 g for simulated diapers) (VWR West-Chester, USA, #28320-041 filter #415). An external pressure (0.7 PSI) was then applied using a circular stainless steel weight (3.13 Kg) having a 9 cm diameter and a height of 7 cm. Alternatively, any weight having a 7 cm diameter and providing a pressure equal to 0.7 PSI or 4.83 KPa may be used. The pressure was maintained for 2 minutes. The increase in weight of the filter papers corresponds to the amount of fluid released by the diapers, C-folds and airlaids.

Penetration Time

The penetration characteristic for C-folds and airlaids was determined using the following method:

A C-fold or an airlaid was placed on a flat surface. A Plexiglas™ plate (19.5 cm×10 cm×0.4 cm) having a circular orifice was positioned on top of the C-fold or airlaid such that the orifice was positioned in the center of the C-fold or airlaid. The circular orifice was then filled with either natural or synthetic blood (7 mL). The chronometer was started as soon as the liquid came into contact with the C-fold or airlaid. Until exhaustion of the liquid, special precautions were taken to ensure that the orifice was always filled with liquid. The chronometer was stopped as soon as all of the liquid had disappeared from the surface of the absorbent article (C-fold or airlaid).

Figure 25:
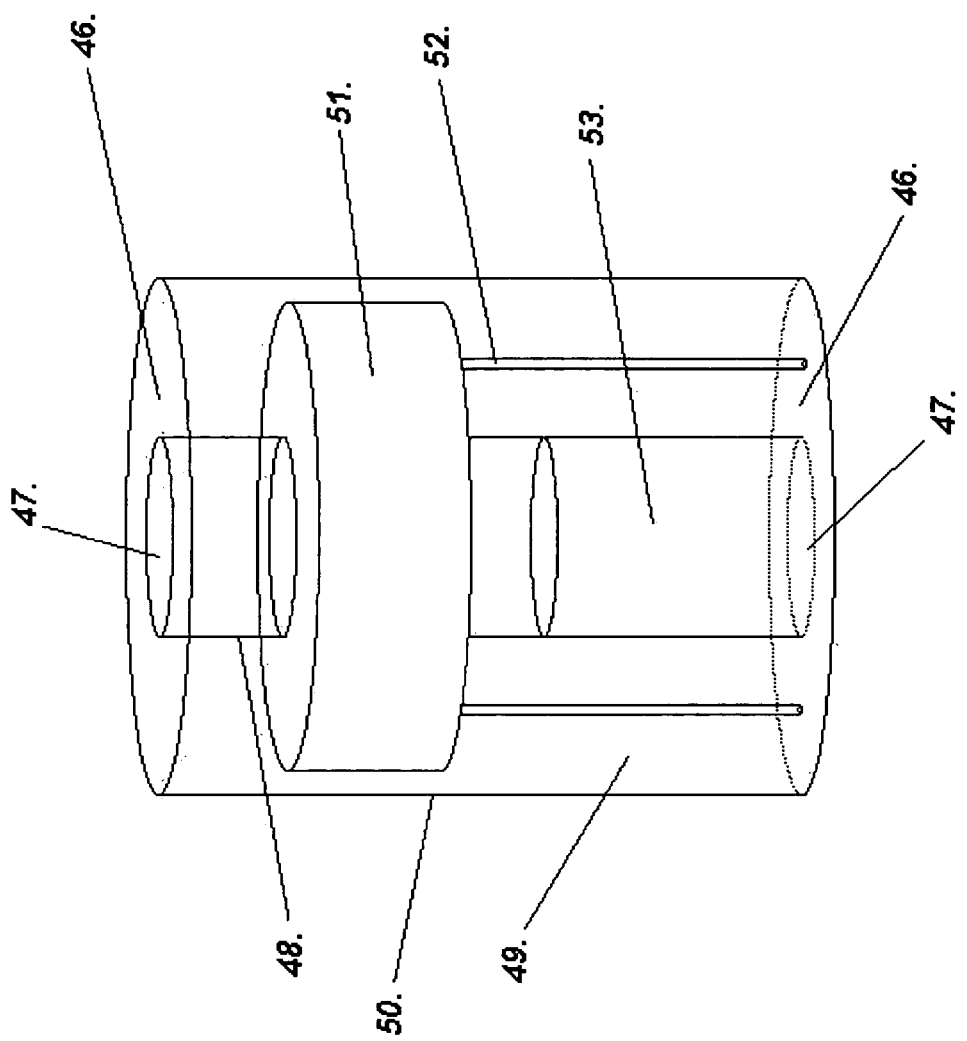
FIG. 25 illustrates a "rewet cylinder", used to measure the rewet characteristics for simulated diapers. The opposing ends of the cylinder (46) are composed of Plexiglas™, and have an orifice (47) measuring 2.5 cm in diameter in their center. Both orifices are connected by an inner cylinder (48), creating a void (49) between the outer cylinder (50) and the inner cylinder (48). A weight (51), supported by two screws (52), is positioned within this void. The weight brings the total mass of the cylinder to 3.87 kg. The inner cylinder (48) is then filled with water (53).

The penetration characteristic for simulated diapers was determined using the following method:

A simulated diaper was placed on a flat surface and the center was marked with a permanent marker. A round Plexiglas™ test cylinder (FIG. 25) was then charged with saline solution (25 mL). The chronometer was started as soon as the liquid came into contact with the simulated diaper. The chronometer was stopped as soon as all of the liquid had disappeared from the surface of the absorbent article (simulated diaper) and the elapsed time was denoted as $T_1$. The cylinder was then charged with an additional amount of saline solution (15 mL) and the chronometer was started as soon as the liquid came into contact with the simulated diaper. The chronometer was stopped as soon as all of the liquid had disappeared from the surface of the absorbent article (simulated diaper) and the elapsed time was denoted as $T_2$. The procedure was repeated a third time using a further 15 mL of saline solution, providing an elapsed time denoted as $T_3$. The penetration time (T) for the simulated diapers is equated as the $T_1+T_2+T_3$.

Diffusion or Stain Area

Following the penetration experiments, the diffusion or stain area of the absorbent articles (C-folds, airlaids and simulated diapers) was analyzed and determined using a multimeter; the multimeter tracing the contour of the moist area left behind on the absorbent articles following exposure to the liquid. The dimensions of the stain were measured and computed.

Scanning Electron Micrographs

Scanning electron micrographs were recorded using an Hitachi® S 3000N scanning electron microscope. Samples were placed on two-sided adhesive paper, glued to an aluminum plate. Any non-glued particles were removed with an air jet. A thin (about 10 nm) gold layer was then applied to the surface of the glued sample by a sputter coater. The surface was then scanned and recorded.

X-Ray Diffraction Spectra

X-ray diffraction spectra were recorded with an X-pert® diffractometer using a Cu Kα source (1.542 Å) (50 KV, 40 mA, scanning rate of 0.02 degree/sec. The Theta-2 Theta method was used to characterize the samples.

Atomic Force Microscopy

Atomic force micrographs were recorded using a Digital Instruments® nanoscope III-A, in tatting mode. Samples were glued to one side of two-sided glued paper. The other side of the glued paper was glued to a magnetic plate, which was secured under the instrument needle.

EXAMPLES

Comparative Example I

Preparation of a Glass-Like Starch

A paste having a total moisture content of 22.8% was prepared by mixing grade A wheat starch (15 Kg) with water (3.7 Kg). The paste was then fed into an extruder using a Ktron™ T35 volumetric feeder rotating at 24 rpm and having the following barrel temperature profile: $Tb_1=32°$ C., $Tb_2=38°$ C., $Tb_3=49°$ C., $Tb_4=66°$ C., $Tb_5=82°$ C., $Tb_6=93°$ C., $Tb_7=104°$ C., and $Tb_8=116°$ C. The flow rate was 16.8 Kg/h, and the extrudate temperature was 129° C. The extruder screw was rotating at 100 rpm. The obtained extrudates were subsequently aged for 24 hours at 60° C. in a convection oven, and ground using a grinder. The ground extrudate was then sieved to provide an extrudate having a particle size ranging from about 150 μm to about 600 μm. The FSC and CRC of the product was determined to be 7.9 g/g and 5.3 g/g respectively. The extrudate particles were analyzed by X-ray diffraction and SEM.

Comparative Example II

Batch Preparation of a Guar Borate

Guar flour (0.5 Kg, Procol P3) was dissolved in 25 liters of water, in a 85 liter mixing vat equipped with a Crepaco® (Rosemont, USA) Liquiverter™ CLV 25 mixer. A 2 liter aqueous solution containing 57 g of Borax was then added to 15.3 Kg of the previously prepared guar mixture (in a 25 liter mixing vat). A firm gel was immediately formed. The gel was thoroughly mixed with a impeller agitator for about 30 minutes, until the gel texture was stabilized. The gel was then separated into 45 samples (382 ml each), which were transferred to Braun® kitchen blenders. Methanol (550-600 mL) was added to each sample followed by stirring for about 1 minute. The pH was adjusted to 7.9 using concentrated hydrochloric acid. The solution was filtered using a Western States® basket centrifuge (1 μm filtering cloth, 3600 rpm). The filtrates were washed with fresh methanol (1.3 L) and dried overnight in a convection oven at 60° C. The resulting powder was ground with a Braun® coffee grinder and sieved, keeping only particles having a size ranging from 122 μm to 559 μm. The material was characterized by X-ray diffraction, AFM and SEM. Various physical characteristics of this borated guar are listed below in Table 3.

TABLE 3

Physical characteristics of the borated guar prepared as described in Comparative example II.

| Characteristic | Results |
| --- | --- |
| Powder | |
| FSC (Saline, g/g) | 105 |
| FSC (Bovine blood, g/g) | 32 |
| FSC (Synthetic blood, g/g) | 34 |
| CRC (Saline, g/g) | 93 |
| CRC (Bovine blood, g/g) | 20 |
| CRC (Synthetic blood, g/g) | 27 |
| AUL (Saline, 0.9 g, 0.7 psi, g/g) | 7.8 |
| AUL (Saline, 0.9 g, 0.9 psi, g/g) | 7.3 |
| Simulated Diaper-Saline | |
| Rewet (g) | 2.88 |
| Penetration time (seconds) | 395 |
| Stain area (cm$^2$) | 160 |
| Airlaid-Bovine blood- | |
| Rewet (g) | 2.06 |
| Penetration time (seconds) | 10.5 |
| Stain area (cm$^2$) | 41.3 |
| C-Fold-Bovine blood | |
| Rewet (g) | 1.43 |
| Penetration time (seconds) | 48 |
| Stain area (cm$^2$) | 42 |
| Airlaid-synthetic blood | |
| Rewet (g) | 2.52 |
| Penetration time (seconds) | 16.8 |
| Stain area (cm$^2$) | 39.2 |
| C-Fold-synthetic blood | |
| Rewet (g) | 1.82 |
| Penetration time (seconds) | 150 |
| Stain area (cm$^2$) | 49.3 |

Example 1

Preparation of a Glass-Like Starch Nanocomposite (9.1% Bentonite)

A paste was prepared by mixing grade A wheat starch (15 Kg), water (4.23 Kg) and bentonite (Bentonite Performance Minerals®; 1.5 Kg). The paste was then fed into an extruder using a Ktron™ T35 volumetric feeder rotating at 22 rpm and having the following barrel temperature profile: $Tb_1=32°$ C., $Tb_2=38°$ C., $Tb_3=49°$ C., $Tb_4=66°$ C., $Tb_5=82°$ C., $Tb_6=93°$ C., $Tb_7=104°$ C., and $Tb_8=116°$ C. The extrusion rate was 13.2 Kg/h, and the extrudate temperature was 122° C. The extruder screw was rotating at 100 rpm. The obtained extrudates were subsequently aged for 24 hours at 60° C. in a convection oven, and ground using a grinder. The ground extrudate was then sieved to provide an extrudate having a particle size ranging from about 150 μm to about 600 μm. The FSC and CRC of the product was determined to be 8.3 g/g and 5.2 g/g respectively. The extrudate particles were analyzed by X-ray diffraction and SEM.

Example 2

Preparation of a Glass-Like Starch Nanocomposite (23.1% Bentonite)

A paste was prepared by mixing grade A wheat starch (15 Kg), water (5.36 Kg) and bentonite (Bentonite Performance Minerals®; 4.5 Kg). The paste was then fed into an extruder using a Ktron™ 35 volumetric feeder rotating at 24 rpm and having the following barrel temperature profile: $Tb_1=32°$ C., $Tb_2=38°$ C., $Tb_3=49°$ C., $Tb_4=66°$ C., $Tb_5=82°$ C., $Tb_6=93°$ C., $Tb_7=104°$ C., and $Tb_8=116°$ C. The extrusion rate was 12.0 Kg/h, and the extrudate temperature was 125.5° C. The extruder screw was rotating at 100 rpm. The obtained extrudates were subsequently aged for 24 hours at 60° C. in a convection oven, and ground using a grinder. The ground extrudate was then sieved to provide an extrudate having a particle size ranging from about 150 μm to about 600 μm. The FSC and CRC of the product was determined to be 7.3 g/g and 3.8 g/g respectively. The extrudate particles were analyzed by X-ray and SEM.

Examples 3 to 6

Comparative Study of the Bentonite Charge Effect in Glass-Like Starch Nanocomposites Pastes were prepared as described in Example 2 and using the parameters illustrated below in Table 4.

TABLE 4

Effect of bentonite concentration in glass-like starch nanocomposites

| Example | Bentonite Kg | Bentonite Dry % (W/W) | Starch (kg) | Water (Kg) | Flow Rate (kg/h) | T (° C.) | FSC (g/g) | CRC (g/g) |
|---|---|---|---|---|---|---|---|---|
| I | 0 | 0 | 15 | 3.7 | 16.8 | 129 | 7.9 | 5.3 |
| 1 | 1.5 | 9.1 | 15 | 4.2 | 13.2 | 122 | 8.3 | 5.2 |
| 3 | 3.0 | 16.7 | 15 | 4.8 | 13.6 | 127 | 8.3 | 4.2 |
| 2 | 4.5 | 23.1 | 15 | 5.36 | 12.0 | 126 | 7.8 | 3.8 |
| 4 | 3.9 | 28.6 | 9 | 4.38 | 19.3 | 121 | 7.2 | 3.0 |
| 5 | 3.9 | 33.3 | 7.8 | 3.35 | 11.9 | 127 | 7.1 | 2.7 |

Synergistic contributions could be determined knowing that bentonite (Bentonite Performance Minerals®) has a FSC of 5.18. The observed synergistic effects are illustrated in Table 5.

TABLE 5

Synergistic contribution of bentonite in glass-like starch nanocomposites.

| Example | Bentonite Dry % (W/W) | Theoretical FSC (g/g) | FSC (g/g) | Synergy (g/g) |
|---|---|---|---|---|
| I | 0 | — | 7.9 | — |
| 1 | 9.1 | 7.6 | 8.3 | 0.7 |
| 3 | 16.7 | 7.4 | 8.3 | 0.9 |
| 2 | 23.1 | 7.3 | 7.8 | 0.5 |
| 4 | 28.6 | 7.1 | 7.2 | 0.1 |
| 5 | 33.3 | 7.0 | 7.1 | 0.1 |

As can be deduced from the synergistic effects shown in Table 5, nanocomposite materials having a bentonite content ranging from about 5 to about 25% are preferred.

Example 7

Batch Preparation of a Borated-Guar Bentonite Nanocomposite (20% Bentonite)

Guar flour (0.5 Kg Procol P3) and bentonite (125 g) (Minelco® Microgel MB 300) were dissolved in 25 liters of water, in a 85 liter mixing vat, equipped with a Crepaco® (Rosemont, USA) Liquiverter™ CLV 25 mixer. A 2 liter aqueous solution containing 57 g of Borax was added to 15.3 Kg of the previously prepared guar mixture (in a 25 liter mixing vat). A firm gel was immediately formed. The gel was thoroughly mixed with a impeller agitator for about 30 minutes, until the gel texture was stabilized. The gel was then separated into 45 samples (384 ml each), which were transferred to Braun® kitchen blenders. Methanol (550-600 mL) was added to each sample followed by stirring for about 1 minute. The pH was adjusted to 7.9 using concentrated hydrochloric acid. The solution was filtered using a Western States® basket centrifuge (1 μm filtering cloth, 3600 rpm). The filtrates were washed with fresh methanol (1.3 L) and dried overnight in a convection oven at 60° C. The resulting powder was ground with a Braun® coffee grinder and sieved, keeping only particles having a size ranging from 122 μm to 559 μm. The material was characterized by X-ray diffraction, AFM and SEM. Various physical characteristics of this borated-guar bentonite nanocomposite material are listed below in Table 6.

TABLE 6

Physical characteristics of the borated guar bentonite nanocomposite material prepared as described in Example 7

| Characteristic | Results |
|---|---|
| Powder characteristics | |
| FSC (Saline, g/g) | 84 |
| FSC (Bovine blood, g/g | 36 |
| FSC (Synthetic blood, g/g) | 43 |
| CRC (Saline, g/g) | 72 |
| CRC (Bovine blood, g/g) | 24 |
| CRC (Synthetic blood, g/g) | 38 |
| AUL (Saline, 0.9 g, 0.7 psi, g/g) | 6.9 |
| AUL (Saline, 0.9 g, 0.9 psi, g/g) | 6.4 |
| Simulated Diaper-Saline | |
| Rewet (g) | 2.67 |
| Penetration time (seconds) | 450 |
| Stain area (cm$^2$) | 174 |
| Airlaid-Bovine blood- | |
| Rewet (g) | 2.75 |
| Penetration time (seconds) | 5 |
| Stain area (cm$^2$) | 35.4 |
| C-Fold-Bovine blood | |
| Rewet (g) | 1.90 |
| Penetration time (seconds) | 18 |
| Stain area (cm$^2$) | 36.3 |
| Airlaid-synthetic blood | |
| Rewet (g) | 2.95 |
| Penetration time (seconds) | 7 |
| Stain area (cm$^2$) | 35.9 |

TABLE 6-continued

Physical characteristics of the borated guar bentonite nanocomposite material prepared as described in Example 7

| Characteristic | Results |
| --- | --- |
| C-Fold-synthetic blood | |
| Rewet (g) | 1.94 |
| Penetration time (seconds) | 110 |
| Stain area (cm$^2$) | 40.8 |

As can be deduced from the data provided in Table 6, the nanocomposite material has a significantly increased FSC and CRC in both natural blood (bovine blood) and synthetic blood, compared to pristine guar-borax. Furthermore, reduced penetration times and increased absorption rates could generally be discerned for the borated-guar bentonite nanocomposite material.

Example 8

Guar-Borate Bentonite Nanocomposite (10% Bentonite)

Guar split (3.00 g; 1.0 equivalent) was suspended in deionized water (150 ml) and stirred with a magnetic stirrer. Sodium hydroxide (30% WN; 3.0 ml; 1.22 equivalents) was then added and the mixture heated at 60° C. for 5 hours. Bentonite (0.334 g; Gray Bentonite, Aldrich) was suspended in distilled water (10 mL) and the resulting suspension stirred at 50° C. The bentonite suspension was then added to the guar slurry and allowed to react for one hour. Boric acid (0.3664 g; 0.32 equivalents), dissolved in deionized water (20 mL), was then added while stirring. The resulting gel was blended with methanol (200 mL), triturated, and transferred into a beaker. The pH was adjusted to 7.91 under vigorous mechanical stirring using hydrochloric acid (10%). The so-obtained solid was filtered, washed with methanol (3×25 ml), dried overnight at 60° C. in a convection oven and ground to provide a white particulate powder having the characteristics shown in Table 7.

TABLE 7

Performance characteristics of the guar-borate bentonite nanocomposite prepared as described in Example 7.

| Guar-borate/bentonite 10% bentonite | Values |
| --- | --- |
| CRC (g/g) | 91 |
| FSC (g/g) | 115 |
| AUL (0.3 psi 0.9 g) (g/g) | 11.0 |
| pH of the gel | 7.4 |

Examples 9-16

Guar-Borate White Bentonite Nanocomposites; Bentonite Charge Effect on the Nanocomposite Materials The guar-borate bentonite nanocomposites of Examples 9-16, were prepared following the procedure previously described in Example 8. White bentonite (Minelco® MB 300) was used. As illustrated below in Table 8, the bentonite charge was varied from 0% to 40% (weight of white bentonite/weight of guar).

TABLE 8

Effect of bentonite concentration on the absorption performance of the nanocomposites.

| Example | White Bentonite Concentration (% W/W) | CRC (g/g) | FSC (g/g) | AUL (0.3 psi 0.9 g) (g/g) | pH of the gel |
| --- | --- | --- | --- | --- | --- |
| 9 | 0% | 93 | 115 | 10.8 | 7.4 |
| 10 | 3% | 95 | 113 | 10.1 | 7.4 |
| 11 | 5% | 90 | 114 | 11.1 | 7.4 |
| 12 | 10% | 74 | 101 | 9.8 | 7.4 |
| 13 | 15% | 73 | 101 | 9.8 | 7.4 |
| 14 | 20% | 76 | 107 | 9.7 | 7.4 |
| 15 | 30% | 60 | 80 | 8.1 | 7.4 |
| 16 | 40% | 61 | 65 | 7.8 | 7.4 |

Example 17

Optimized Guar-Phosphate/Gray Bentonite Nanocomposite (10% Bentonite)

Guar split (5.0 g) was suspended in deionized water (167 mL) and stirred with a magnetic stirrer. Bentonite (0.56 g; Gray Bentonite, Aldrich) was suspended in distilled water (10 mL) and the resulting suspension stirred at 50° C. The bentonite suspension was then added to the guar slurry and allowed to react for one hour. Sodium hydroxide (30% WN; 6.0 ml; 1.46 equivalents) was then added, followed by the addition of sodium tripolyphosphate (STPP; 0.16 g; 0.0141 equivalents) and the mixture heated to 70° C. for 15 hours. After cooling to room temperature, the resulting gel was blended with methanol (200 mL), triturated, and transferred into a beaker. The pH was adjusted to 7.41 under vigorous mechanical stirring using a hydrochloric acid solution (10%). The so-obtained solid was filtered, washed with methanol (3×50 ml), dried overnight at 60° C. in a convection oven and ground to provide a white particulate powder having the characteristics shown in Table 9.

TABLE 8

Performance characteristics of the guar-phosphate bentonite nanocomposite prepared as described in Example 17.

| Guar-phosphate/bentonite 10% bentonite | Values |
| --- | --- |
| CRC (g/g) | 39 |
| FSC (g/g) | 48 |
| AUL (0.3 psi 0.9 g) (g/g) | 9.0 |
| pH of the gel | 7.4 |

Examples 18-21

Guar-phosphate Gray Bentonite Nanocomposites; Bentonite Charge Effect on the Nanocomposite Materials The guar-phosphate bentonite nanocomposites of Examples 18-21, were prepared following the procedure previously described on Example 17. As illustrated below in Table 10, the bentonite charge was varied from 0% to 40% (weight of gray bentonite/weight of guar).

TABLE 10

Effect of bentonite concentration on the absorption performance of the guar-phosphate bentonite nanocomposites.

| Example | Gray Bentonite Concentration (% W/W) | CRC (g/g) | FSC (g/g) | AUL (0.3 psi 0.9 g) (g/g) | pH of the gel |
|---|---|---|---|---|---|
| 18 | 0% | 48 | 61 | 9.4 | 7.4 |
| 19 | 20% | 37 | 51 | 10.0 | 7.4 |
| 20 | 30% | 19 | 29 | 10.0 | 7.4 |
| 21 | 40% | 17 | 22 | 10.0 | 7.4 |

Examples 22-26

Guar-Borax White Bentonite Nanocomposites; Bentonite Charge Effect on the Nanocomposite Materials Using a High Shear Mixer White bentonite [Minelco® MB 300; 0,334 g (10%); 0,755 g (20%); 1.29 g (30%); 2.00 g (40%)] was suspended in deionized water (150 ml) and heated at 70° C. Upon cooling to room temperature, guar flour (3.00 g; Procol®) was added. The resulting solution was stirred using a Silverson® High-Shear mixer (30 minutes at 8000 rpm). A borax solution (20 mL; 5.65 g of borax in 200 ml of deionized water) was then added, and the resulting gel stirred for 25 minutes. The resulting gels were blended with methanol (350 mL), triturated, and transferred into a beaker. The pH was adjusted to 7.90 under vigorous mechanical stirring using hydrochloric acid (10%). The so-obtained solid was filtered, washed with methanol (3×50 ml), dried overnight at 60° C. in a convection oven and ground to provide a white particulate powder having the characteristics shown in Table 11. As illustrated below in Table 11, the bentonite charge was varied from 0% to 40% (weight of gray bentonite/weight of guar).

TABLE 11

Performance characteristics of the guar-borate bentonite nanocomposite prepared using a high shear mixer.

| Example | Gray Bentonite Concentration (% W/W) | CRC (g/g) | FSC (g/g) |
|---|---|---|---|
| 22 | 0% | 100 | 84 |
| 23 | 10% | 122 | 100 |
| 24 | 20% | 76 | 55 |
| 25 | 30% | 78 | 62 |
| 26 | 40% | 72 | 58 |

Examples 27-30

Guar-Borate Celite Nanocomposites

The guar-borate celite nanocomposites of Examples 27-30, were prepared following the procedure previously described in Example 8. Celite (Aldrich) was used in place of gray bentonite. As illustrated below in Table 12, the celite charge was varied from 0% to 40% (weight of celite/weight of guar).

TABLE 12

Effect of celite charge on the absorption performance of the guar-borate celite nanocomposites.

| Example | Celite Concentration (% W/W) | CRC (g/g) | FSC (g/g) | AUL (0.3 psi 0.9 g) (g/g) | pH of the gel |
|---|---|---|---|---|---|
| 9 | 0% | 93 | 115 | 10.8 | 7.4 |
| 27 | 10% | 93 | 94 | 11.7 | 7.4 |
| 28 | 20% | 57 | 95 | 10.0 | 7.4 |
| 29 | 30% | 43 | 83 | 9.2 | 7.4 |
| 30 | 40% | 28 | 58 | 8.4 | 7.4 |

Examples 31-33

Guar-borate Laponite™ Nanocomposites

Laponite™ [0,187 g (3%); 0,316 g (5%)] was suspended in deionized water (150 ml) and heated at 70° C. Upon cooling to room temperature, guar flour (6.00 g; Procol®) was added. A borax solution (40 mL; 5.65 g of borax in 200 ml of deionized water) was then added, and the resulting gel stirred for 25 minutes. The resulting gels were blended with methanol (700 mL), triturated, and transferred into a beaker. The pH was adjusted to 7.90 under vigorous mechanical stirring using hydrochloric acid (10%). The so-obtained solid was filtered, washed with methanol (3×100 ml), dried overnight at 60° C. in a convection oven and ground to provide a white particulate powder having the characteristics shown in Table 13. As illustrated below in Table 13, the Laponite™ charge was varied from 0% to 5% (weight of Laponite™/weight of guar).

TABLE 13

Effect of Laponite ™ charge on the absorption performance of the guar-borate Laponite ™ nanocomposites.

| Example | Laponite ™ Concentration (% w/w) | CRC (g/g) | FSC (g/g) | AUL (0.9 g, 0.7 PSI) |
|---|---|---|---|---|
| 31 | 0% | 97 | 75 | 7.65 |
| 32 | 3% | 93 | 76 | 7.51 |
| 33 | 5% | 95 | 77 | 7.44 |

Examples 34-36

Guar-Borate Illite Nanocomposites

Illite [0,187 g (3%); 0,316 g (5%)] was suspended in deionized water (150 ml) and heated at 70° C. Upon cooling to room temperature, guar flour (6.00 g; Procol®) was added. A borax solution (40 mL; 5.65 g of borax in 200 ml of deionized water) was then added, and the resulting gel stirred for 25 minutes. The resulting gels were blended with methanol (700 mL), triturated, and transferred into a beaker. The pH was adjusted to 7.90 under vigorous mechanical stirring using hydrochloric acid (10%). The so-obtained solid was filtered, washed with methanol (3×100 ml), dried overnight at 60° C. in a convection oven and ground to provide a white particulate powder having the characteristics shown in Table 14. As illustrated below in Table 14, the illite charge was varied from 0% to 5% (weight of illite/weight of guar).

TABLE 14

Effect of illite charge on the absorption performance of the guar-borate illite nanocomposites.

| Example | Illite Concentration (% W/W) | CRC (g/g) | FSC (g/g) | AUL (0.9 g, 0.7 PSI) |
|---|---|---|---|---|
| 34 | 0% | 96.73 | 75.43 | 7.65 |
| 35 | 3% | 77.20 | 61.54 | 6.45 |
| 36 | 5% | 103.59 | 83.62 | 4.60 |

Examples 37-39

Absorption Kinetics of Guar-Borate Bentonite Nanocomposites

Bentonite [Minelco® MB 300; Example 37: 0% (pristine guar-borate); Example 38: 1.87 g (30%); Example 39: 2.49 g (40%)] was suspended in deionized water (150 mL) and heated at 70° C. for 30 minutes. Upon cooling to room temperature, guar flour (6.00 g; Procol®) was added. The resulting solution was stirred for 45 minutes. A borax solution (40 mL; 5.65 g of borax in 200 ml of deionized water) was then added, and the resulting gel stirred for 25 minutes. The resulting gels were blended with methanol (700 mL), triturated, and transferred into a beaker. The pH was adjusted to 7.90 under vigorous mechanical stirring using hydrochloric acid (10%). The so-obtained solid was filtered, washed with methanol (3×100 ml), dried overnight at 60° C. in a convection oven and ground to provide a white particulate powder. In the course of the FSC measurements, the tea bags were exposed to a saline solution for defined periods of time (5 minutes, 10 minutes, 15 minutes, 30 minutes, 1 hour, 1½ hour, 2 hours, 2½ hours and 3 hours). From the results illustrated in FIG. 24, it can be observed that pristine guar-borax exhibits a maximum absorption at 30 minutes. However, the absorption capacity diminished somewhat in the next 30 minutes, indicative of syneresis and gel flowing problems. In contrast to pristine guar-borate, the guar-borate bentonite nanocomposites did not suffer from any syneresis and gel flowing problems.

Example 40-41

Figure 22:
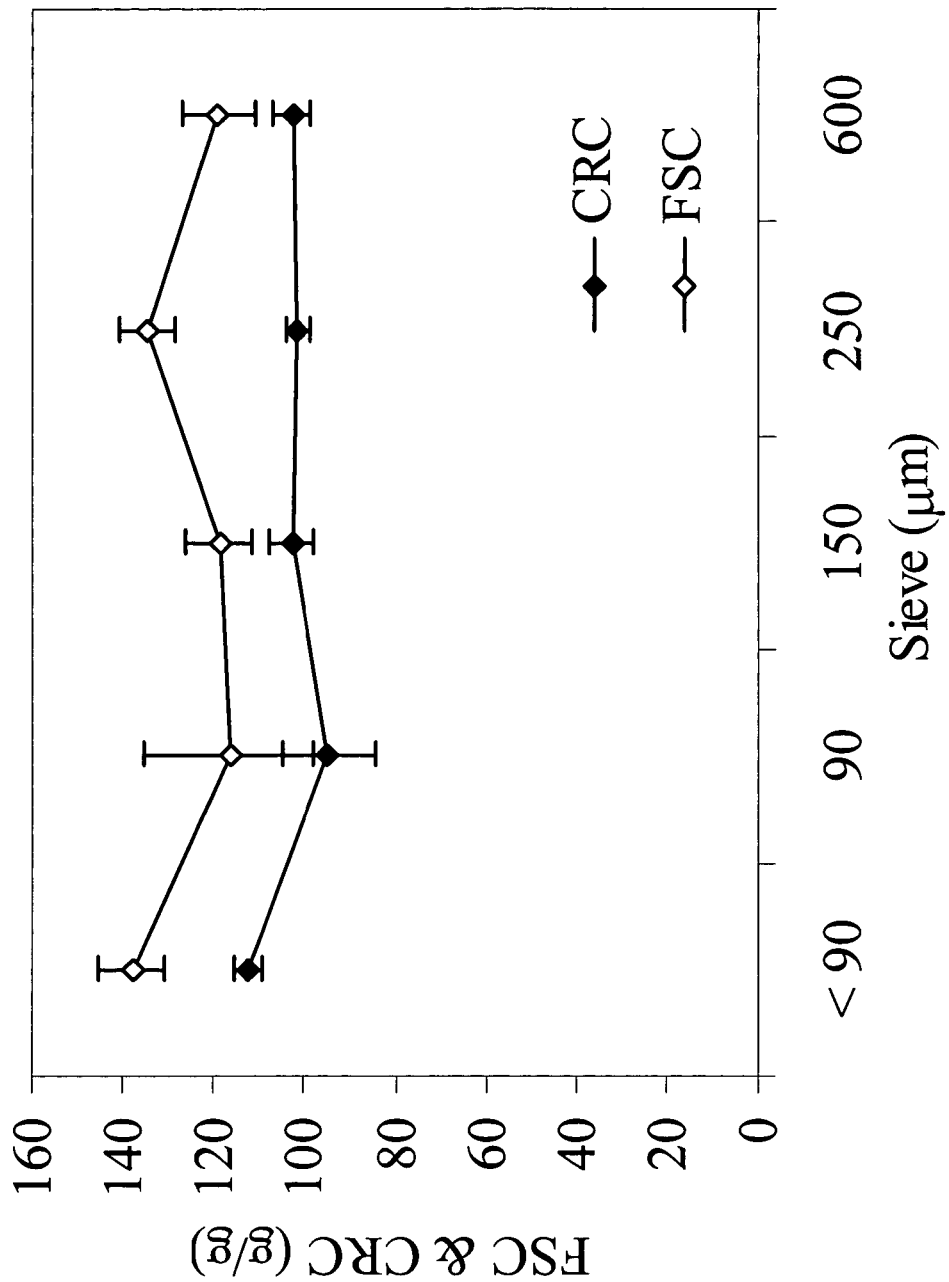
FIG. 22 illustrates the FSC and CRC behavior of a guar-borax nanocomposite (3% bentonite), as a function of particle size distribution.
Figure 23:
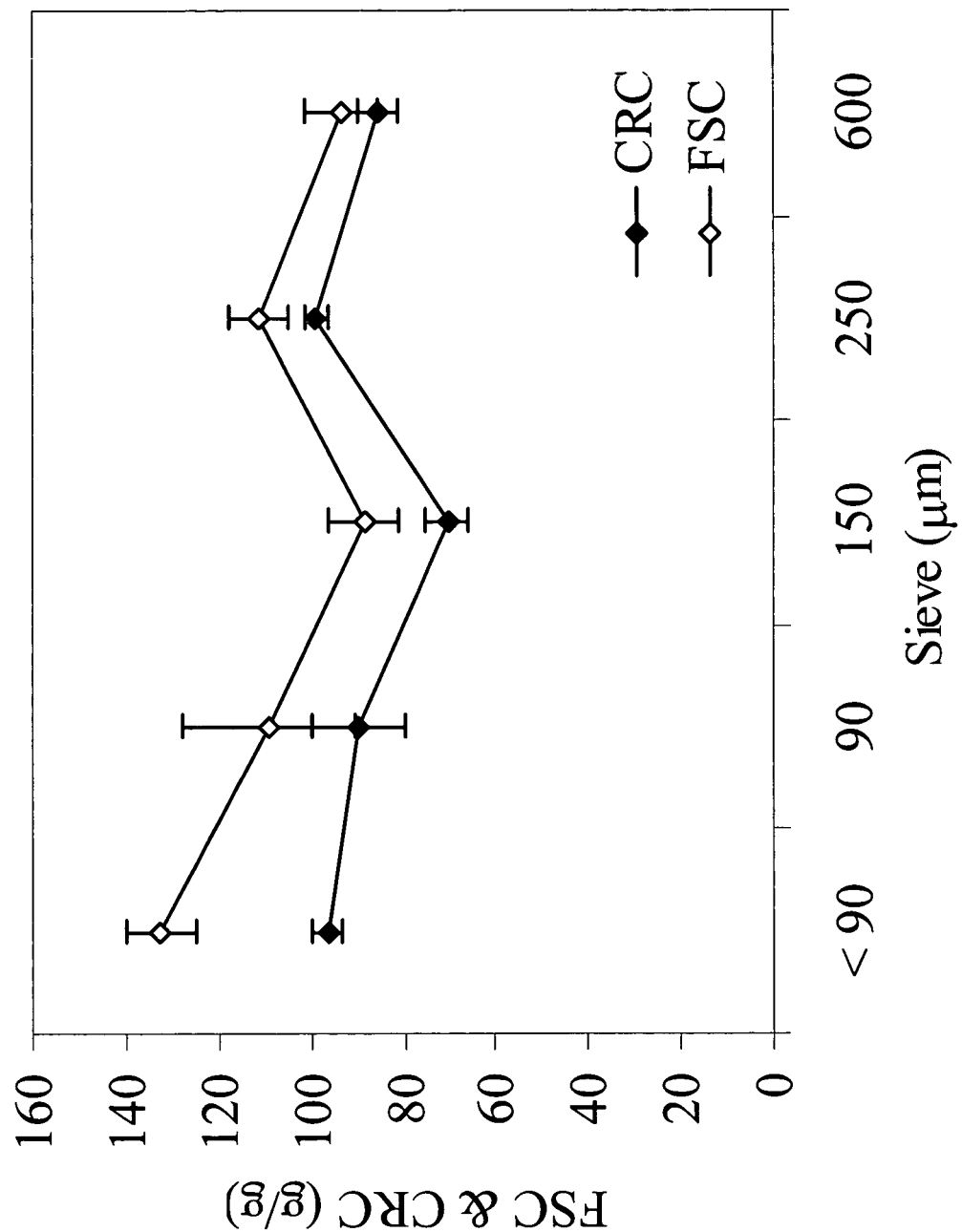
FIG. 23 illustrates the FSC and CRC behavior of pristine guar-borax as a function of particle size distribution.

Guar-Borate Bentonite Nanocomposites; Effect of Particle Size on the Absorption Performance White bentonite [Minelco® MB 300; Example 40: 0% (pristine guar-borate); Example 41: 0.373 g (3%)] was suspended in deionized water (600 mL) and heated at 70° C. for 30 minutes. Upon cooling to room temperature, guar gum (12.0 g; Procol®, 1 equivalent) was added. The resulting solution was stirred for 45 minutes. A borax solution (80 mL; 0.074N, 0.08 equivalents) was then added, and the resulting gel stirred for 25 minutes. The resulting gels were blended with methanol (1200 mL), triturated, and transferred into a beaker. The pH was adjusted to 7.90 under vigorous mechanical stirring using a hydrochloric acid solution (10%). The so-obtained solid was filtered, washed with methanol (3×50 ml), dried overnight at 60° C. in a convection oven and ground to provide a white particulate powder. The resulting powder was sieved using Mesh 30, 60, 100 and 170 sieves. The FSC, CRC and AUL was determined for each sieving product. The results obtained for pristine guar-borate (Example 40) and the guar-borate bentonite nanocomposite (Example 41) are illustrated in FIGS. 23 and 22 respectively. From the results illustrated in FIG. 22 it can be observed that the guar-borate bentonite nanocomposite exhibits essentially stable FSC and CRC characteristics throughout the particle range distribution. However, pristine guar borate exhibits reduced FSC and CRC characteristics for particles having a size of about 150 µm (FIG. 23).

Example 42-45

Synergistic Effects in Guar-Borate Bentonite Nanocomposites

White bentonite [Minelco® MB 300; 0.094 g (3%); 0.188 g (5%); 0.316 g (10%)] was suspended in deionized water (150 ml) and heated at 70° C. Upon cooling to room temperature, guar flour (3.00 g; Procol®) was added. A borax solution (20 mL; 5.65 g of borax in 200 ml of deionized water) was then added, and the resulting gel stirred for 25 minutes. The resulting gels were blended with methanol (350 mL), triturated, and transferred into a beaker. The pH was adjusted to 7.90 under vigorous mechanical stirring using hydrochloric acid (10%). The so-obtained solid was filtered, washed with methanol (3×50 ml), dried overnight at 60° C. in a convection oven and ground to provide a white particulate powder having the characteristics shown in Table 15. As illustrated below in Table 15, the bentonite charge was varied from 0% to 10%.

TABLE 13

Performance characteristics of the guar-borate bentonite nanocomposite prepared using various bentonite charges.

| Example | % Dry bentonite (w/w) | FSC found (g/g) | CRC found (g/g) | FSC calculated (g/g) | CRC calculated (g/g) | FSC synergy (g/g) | CRC synergy (g/g) |
|---|---|---|---|---|---|---|---|
| 42 | 0 | 111 | 98 | — | — | — | — |
| 43 | 3 | 135 | 102 | 108 | 95 | 27 | 7 |
| 44 | 5 | 132 | 101 | 106 | 93 | 26 | 8 |
| 45 | 10 | 103 | 91 | 100 | 88 | 3 | 3 |

Although the present invention has been described hereinabove by way of preferred embodiments thereof, it can be modified without departing from the spirit and nature of the subject invention as defined in the appended claims.

The invention claimed is:

1. An absorbent or a superabsorbent nanocomposite particle, said particle comprising a nanocomposite material that includes a nanoscale dispersion of delaminated phyllosilicates dispersed throughout a polysaccharide network, said delaminated phyllosilicates are present in a range from about 1% (w/w) to about 40% (w/w), wherein the size of said particle ranges front 88 µm to 590 µm and said polysaccharide network is a glass-like polysaccharide or a cross-linked polysaccharide.

2. The nanocomposite particle of claim 1, herein the polysaccharide is a biodegradable polysaccharide.

3. The nanocomposite particle of claim 2, herein the biodegradable polysaccharide is selected from the group consisting of starch, modified starches, amylopectin, modified amylopectin, amylose, modified amylose, chitosan, modified chithosan, chitin, modified chitin, guar gum, modified guar gum, locust bean gum, modified locust bean gum, tarn gum, modified tarn gum, konjac, modified konjac, fenugreek gum, modified fenugreek gum, mesquite gum, modified mesquite gum, aloe mannans, modified aloe mannans, carboxyalkylated cellulose, carboxymethyl cellulose, oxidized polysaccharides, sulfated polysaccharides, cationic polysaccharides, pectin, arabic gum, karaya gum, xanthan, kappa, iota or lambda carrageenans, agar-agar, alginates and combinations thereof.

4. The nanocomposite particle of claim 1, wherein the polysaccharide is selected from the group consisting of guar and starch.

5. The nanocomposite particle of claim 4, wherein the guar is a crosslinked guar.

6. The nanocomposite particle of claim 4, wherein the starch is a glass-like starch.

7. The nanocomposite particle of claim 5, wherein the crosslinked guar is crosslinked with crosslinking agents selected from the group consisting of borax, bode acid, borates, glyoxal, epichlorohydrin, sodium trimetaphosphate, sodium tripolyphosphate, phosphorous oxychloride, succinyl dichloride, acryloyl chloride, butanediol diglycidyl ether, ethanedioldiglycidyl ether, pyromellitic dianhydride, divinylsulfones, diisocyanates, alkylene bisacrylamides and mixtures thereof.

8. The nanocomposite particle of claim 7, wherein the crosslinking agents are selected from the group consisting of borax, boric acid borates and combinations thereof.

9. The nanocomposite particle of claim 1, wherein the phyllosilicate is exfoliated or semi-exfoliated clay.

10. The nanocomposite particle of claim 9, wherein the clay is selected from the group consisting of smectites, hectorites, bentonites, montmorillonites, synthetic layered silicate, celites, illites and mixtures thereof.

11. The nanocomposite particle of claim 10, wherein the clay is a bentonite.

12. The nanocomposite particle of claim 11, wherein the bentonite is selected from the group consisting of calcium bentonite, sodium bentonite, magnesium bentonite and potassium bentonite.

13. The nanocomposite particle of claim 9, wherein the phyllosilicate is an exfoliated clay.

14. The nanocomposite particle of claim 9, wherein the phyllosilicate is a semi-exfoliated clay.

15. The nanocomposite particle of claim 11, comprising a phyllosilicate content ranging from about 1 to about 25% (w/w).

16. The nanocomposite particle of claim 1, wherein the nanocomposite material is comprised in a product selected from the group consisting of diapers, incontinence articles, feminine hygiene products, airlaids, absorbent dressings, household articles, sealing materials, humectants for agricultural products for soil conditioning, anti-condensation coatings, water-storing materials in agriculture/horticulture/forestry, absorbent paper products, bandages and surgical pads, absorbents for chemical spills polymeric gels for cosmetics and pharmaceuticals, and artificial snow.

17. The nanocomposite particle of claim 1, wherein the nanocomposite particle is a superabsorbent material.

18. A composition comprising an absorbent nanocomposite particle as defined in claim 1, and at least one co-absorbent material.

19. The composition of claim 18, wherein the co-absorbent material is selected from the group consisting of synthetic superabsorbent polymers, mannose-based polysaccharides, ionic polysaccharides, fibers and mixtures thereof.

20. The composition of claim 19, wherein the synthetic superabsorbent polymers are based on monomers selected from the group consisting of acrylic acid, acrylate salts, acrylic ester, acrylic anhydride, methacrylic acid, methacrylate salts, methacrylic esters, methacrylic anhydride, maleic anhydride, maleic salts, maleate esters, acrylamide acrylonitrile, vinyl alcohol, vinyl pyrrolidone, vinyl acetate, vinyl guanidin, aspartic acid, aspartic salts and mixtures thereof.

21. The composition of claim 19, wherein the mannose based polysaccharides are selected from the group consisting of guar gum, tarn gum, locust bean gum, konjac, mesquite gum, fenugreek gum and mixtures thereof.

22. The composition of claim 19, wherein the ionic polysaccharides are selected from the group consisting of carboxyalkyl polysaccharides, carboxymethyl cellulose, carboxymethyl starch, oxidized polysaccharides, xanthan, carrageenans, pectin and mixtures thereof.

23. The composition of claim 19, wherein the fibers are selected from the group consisting of cellulose, viscose, rayon, cellulose acetate, nylon, polyalkylenes, polyethylene, polypropylene, bi-component fibers, polyesters, polylactides, polypropanediols, lyocell, sphagnum and mixtures thereof.

24. The composition of claim 18, wherein the composition is comprised in a product selected from the group consisting of diapers, incontinence articles, feminine hygiene products, airlaids, absorbent dressings, household articles, sealing materials, humectants for agricultural products for soil conditioning, anti-condensation coatings, water-storing materials in agricultural/horticulture/forestry, an absorbent paper products, bandages and surgical pads, absorbents for chemical spills, polymeric gels for cosmetics and pharmaceuticals, and artificial snow.

25. An article of manufacture comprising the absorbent or a superabsorbent nanocomposite particle of claim 1.

26. The article of manufacture of claim 25, wherein the article of manufacture is selected from the group consisting of a diaper, an incontinence article, a feminine hygiene product, an airlaid, an absorbent dressing, a household article, a sealing material, a humectant for agricultural products for soil conditioning, an anti-condensation coating, a water-storing material in agriculture/horticulture/forestry, an absorbent paper product, a bandage or surgical pad, an absorbent for chemical spills, a polymeric gel for cosmetics and pharmaceuticals, and artificial snow.

27. The article of manufacture of claim 26, wherein the article of manufacture is a diaper, an incontinence article, or a feminine hygiene product.

28. The article of manufacture of claim 25, wherein the article of manufacture further comprises at least one co-absorbent material.

29. The article of manufacture of claim 28, wherein the co-absorbent material is selected from the group consisting of a synthetic superabsorbent polymer, a mannose-based polysaccharide, an ionic polysaccharide, a fiber and mixtures thereof.

30. The nanocomposite particle of claim 1, wherein the delaminated phyllosilicates are uniformly dispersed throughout the polysaccharide network.

31. An absorbent or a superabsorbent nanocomposite particle comprising a nanoscale dispersion of delaminated phyllosilicates dispersed throughout a polysaccharide network, said delaminate phyllosilicates are present in a range from about 1% (w/w) to about 40% (w/w), wherein said particle exhibits:
(a) a size ranging from 88 μm to 590 μm and
(b) the presence of a shouldering at 4° theta when analyzed by X-Ray diffraction.

32. The absorbent or superabsorbent nanocomposite particle of claim 31, wherein the average interlayer spacing between each phyllosilicate corresponds to 20-25 Angstroms.

33. An absorbent or a superabsorbent nanocomposite particle comprising a nanoscale dispersion of delaminated phyllosilicates dispersed throughout a polysaccharide network, said delaminated phyllosilicates are present in a range from about 1% (w/w) to about 40% (w/w), wherein said particle exhibits:
(a) a size ranging from 88 μm to 590 μm; and
(b) said delaminated phyllosilicates comprising from 45 to 70 phyllosilicate, blocks.

34. An absorbent or a superabsorbent nanocomposite particle comprising a nanoscale dispersion of delaminated phyllosilicates blocks dispersed throughout a polysaccharide network, said delaminated phyllosilicates are present in a range from about 1% (w/w) to about 40% (w/w), wherein said particle exhibits:
(a) a size ranging from 88 μm to 590 μm; and
(b) said phyllosilicates blocks having a thickness of about 50 nm.

35. An absorbent or superabsorbent nanocomposite particle, said particle comprising a nanocomposite material that includes a nanoscale dispersion of delaminated phyllosilicates dispersed throughout a polysaccharide network, said delaminated phyllosilicates are present in a range from about 1% (w/w) to about 40% (w/w), wherein the size of said particle ranges from 88 μm to 590 μm, said polysaccharide network is a glass-like polysaccharide or a cross-linked polysaccharide, and wherein said delaminated phyllosilicates are, exfoliated or semi-exfoliated clay.

36. An absorbent or a superabsorbent nanocomposite particle, said particle comprising a nanoscale dispersion of delaminated phyllosilicates dispersed throughout a polysaccharide network, said delaminated phyllosilicates are present in a range from about 1% (w/w) to about 40% (w/w), wherein the size of said particle ranges from 88 μm to 590 μm and said polysaccharide network is a glass-like polysaccharide or a cross-linked polysaccharide, and wherein said nanocomposite particle is produced by mixing swollen hydrated clays with a starch paste followed by extrusion of the clay-starch mixture.

* * * * *